US011307197B2

(12) United States Patent
Zhang et al.

(10) Patent No.: US 11,307,197 B2
(45) Date of Patent: Apr. 19, 2022

(54) POLYARGININE-COATED MAGNETIC NANOVECTOR AND METHODS OF USE THEREOF

(71) Applicant: University of Washington through its Center for Commercialization, Seattle, WA (US)

(72) Inventors: Miqin Zhang, Bothell, WA (US); Omid Veiseh, Kirkland, WA (US); Chen Fang, Lynnwood, WA (US); Forrest Kievit, Brier, WA (US)

(73) Assignee: University of Washington, Seattle, WA (US)

( * ) Notice: Subject to any disclaimer, the term of this patent is extended or adjusted under 35 U.S.C. 154(b) by 673 days.

(21) Appl. No.: 15/012,617

(22) Filed: Feb. 1, 2016

(65) Prior Publication Data

US 2016/0153976 A1  Jun. 2, 2016

Related U.S. Application Data

(62) Division of application No. 13/893,137, filed on May 13, 2013, now abandoned.

(60) Provisional application No. 61/646,101, filed on May 11, 2012.

(51) Int. Cl.
| | |
|---|---|
| *G01N 33/543* | (2006.01) |
| *A61K 49/18* | (2006.01) |
| *G01N 33/58* | (2006.01) |
| *A61K 47/34* | (2017.01) |
| *A61K 9/50* | (2006.01) |
| *C12N 15/113* | (2010.01) |
| *C12N 15/85* | (2006.01) |

(52) U.S. Cl.
CPC ..... *G01N 33/54346* (2013.01); *A61K 9/5031* (2013.01); *A61K 47/34* (2013.01); *A61K 49/186* (2013.01); *A61K 49/1872* (2013.01); *C12N 15/113* (2013.01); *C12N 15/85* (2013.01); *G01N 33/582* (2013.01); *A61K 9/5094* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 7,462,446 | B2 | 12/2008 | Zhang et al. |
| 7,666,394 | B2 | 2/2010 | Zhang et al. |
| 8,460,692 | B2 | 6/2013 | Zhang et al. |
| 2006/0105052 | A1 | 5/2006 | Acar et al. |
| 2006/0251613 | A1 | 11/2006 | Zhang et al. |
| 2008/0213377 | A1* | 9/2008 | Bhatia ................... A61K 47/62 424/489 |
| 2008/0226562 | A1 | 9/2008 | Groves et al. |
| 2009/0011004 | A1 | 1/2009 | Lutz et al. |
| 2009/0123366 | A1 | 5/2009 | Dobson et al. |
| 2010/0260686 | A1 | 10/2010 | Zhang et al. |
| 2011/0229576 | A1 | 9/2011 | Trogler et al. |
| 2012/0157626 | A1 | 6/2012 | Wang et al. |
| 2012/0207795 | A1 | 8/2012 | Zink et al. |
| 2013/0189367 | A1 | 7/2013 | Zhang et al. |

FOREIGN PATENT DOCUMENTS

WO    2012/075533 A1    6/2012

OTHER PUBLICATIONS

Akhtar, S., and I. Benter, "Toxicogenomics of Non-Viral Drug Delivery Systems for RNAi: Potential Impact on siRNA-Mediated Gene Silencing Activity and Specificity," Advanced Drug Delivery Reviews 59(2-3):164-182, Mar. 2007.
Bareford, L.M., and P.W. Swaan, "Endocytic Mechanisms for Targeted Drug Delivery," Advanced Drug Delivery Reviews 59(8):748-758, Aug. 2007.
Bumcrot, D., et al., "RNAi Therapeutics: A Potential New Class of Pharmaceutical Drugs," Nature Chemical Biology 2(12):711-719, Dec. 2006.
Fang, C., et al., "Functionalization of Iron Oxide Magnetic Nanoparticles With Targeting Ligands: Their Physicochemical Properties and In Vivo Behavior," Nanomedicine (Lond) 5(9):1357-1369, Nov. 2010.
Fang, C., et al., "Functionalized Nanoparticles With Long-Term Stability in Biological Media," Small 5(14):1637-1641, Jul. 2009.
Futaki, S., "Membrane-Permeable Arginine-Rich Peptides and the Translocation Mechanisms," Advanced Drug Delivery Reviews 57(4):547-558, Feb. 2005.
Haglund, E., et al., "Design of Multifunctional Nanomedical Systems," Annals of Biomedical Engineering 37(10):2048-2063, Oct. 2009.
Hunter, A.C., "Molecular Hurdles in Polyfectin Design and Mechanistic Background to Polycation Induced Cytotoxicity," Advanced Drug Delivery Reviews 58(14):1523-1531, Dec. 2006.
Jung, J., et al., "Selective Inhibition of Human Brain Tumor Cells Through Multifunctional Quantum-Dot-Based siRNA Delivery," Angewandte Chemie International Edition 49(1):103-107, Jan. 2010.
Kievit, F.M., et al., "PEI-PEG-Chitosan-Copolymer-Coated Iron Oxide Nanoparticles for Safe Gene Delivery Synthesis, Complexation, and Transfection," Advanced Functional Materials 19(14):2244-2251, Jul. 2009.
Kim, D.H., and J.J. Rossi, "Strategies for Silencing Human Disease Using RNA Interference," Nature Reviews Genetics 8(3):173-184, Mar. 2007.

(Continued)

Primary Examiner — Jennifer Lamberski
(74) Attorney, Agent, or Firm — Christensen O'Connor Johnson Kindness PLLC

(57) ABSTRACT

Polyarginine-coated nanoparticle, and methods for making and using the nanoparticle. The nanoparticle can have a core that includes a material that imparts magnetic resonance imaging activity to the particle and, optionally, include one or more of an associated therapeutic agent, targeting agent, and diagnostic agent.

13 Claims, 16 Drawing Sheets
Specification includes a Sequence Listing.

(56) References Cited

OTHER PUBLICATIONS

Lee, J.-H., et al., "All-in-One Target-Cell-Specific Magnetic Nanoparticles for Simultaneous Molecular Imaging and siRNA Delivery," Angewandte Chemie International Edition 48(23):4174-4179, May 2009.
Lee, J.-S., et al., "Gold, Poly(β-amino ester) Nanoparticles for Small Interfering RNA Delivery," Nano Letters 9(6):2402-2406, Jun. 2009.
Longmire, M., et al., "Clearance Properties of Nano-Sized Particles and Molecules as Imaging Agents: Considerations and Caveats," Nanomedicine (Lond) 3(5):703-717, Oct. 2008. (Author manuscript provided PMCID: PMC3407669, available in PMC Jul. 29, 2012, 21 pages.).
Martin, M.E., and K.G. Rice, "Peptide-Guided Gene Delivery," AAPS Journal 9(1):E18-E29, Feb. 2007.
Medarova, Z., et al., "In Vivo Imaging of siRNA Delivery and Silencing in Tumors," Nature Medicine 13(3):372-377, Mar. 2007.
Mok, H., et al., "Enhanced Intracellular Delivery of Quantum Dot and Adenovirus Nanoparticles Triggered by Acidic pH Via Surface Charge Reversal," Bioconjugate Chemistry 19(4):797-801, Apr. 2008.
Mok, H., et al., "Multimeric Small Interfering Ribonucleic Acid for Highly Efficient Sequence-Specific Gene Silencing," Nature Materials 9(3):272-278, Mar. 2010.
Mok, H., et al., "pH-Sensitive siRNA Nanovector for Targeted Gene Silencing and Cytotoxic Effect in Cancer Cells," Molecular Pharmaceutics 7(6):1930-1939, Dec. 2010.
Pecot, C.V., et al., "RNA Interference in the Clinic: Challenges and Future Direction," Nature Reviews: Cancer 11(1):59-67, Jan. 2011.
Schmidt, N., et al., "Arginine-Rich Cell-Penetrating Peptides," FEBS Letters 584(9):1806-1813, May 2010.
Singh, N., et al., "Effect of Nanoparticle Conjugation on Gene Silencing by RNA Interference," Journal of the American Cancer Society (JACS) Communications 132(24):8241-8243, Jun. 2010.
Song, W.-J., et al., "Gold Nanoparticles Capped With Polyethyleneimine for Enhanced siRNA Delivery," Small 6(2):239-246, Jan. 2010.
Veiseh, M., et al., "Tumor Paint: A Chlorotoxin:Cy5.5 Bioconjugate for Intraoperative Visualization of Cancer Foci," Cancer Research 67(14):6882-6888, Jul. 2007.
Veiseh, O., et al., "Cell Transcytosing Poly-Arginine Coated Magnetic Nanovector for Safe and Effective siRNA Delivery," Biomaterials 32(24):5717-5725, Aug. 2011.
Veiseh, O., et al., "Design and Fabrication of Magnetic Nanoparticles for Targeted Drug Delivery and Imaging," Advanced Drug Delivery Reviews 62(3):284-304, Mar. 2010.
Veiseh, O., et al., "A Ligand-Mediated Nanovector for Targeted Gene Delivery and Transfection in Cancer Cells," Biomaterials 30(4):649-657, Feb. 2009.
Veiseh, O., et al., "Optical and MRI Multifunctional Nanoprobe for Targeting Gliomas," Nano Letters 5(6):1003-1008, Jun. 2005.
Veiseh, O., et al., "Specific Targeting of Brain Tumors With an Optical/Magnetic Resonance Imaging Nanoprobe Across the Blood-Brain Barrier," Cancer Research 69(15):6200-6207, Aug. 2009.
Vorhies, J.S., and J.J. Nemunaitis, "Synthetic vs. Natural/Biodegradable Polymers for Delivery of shRNA-Based Cancer Therapies," in M. Belting (ed.), "Methods in Molecular Biology: Macromolecular Drug Delivery," Humana Press, New York, 2009, vol. 480, Chap. 2, pp. 11-29.
Whitehead, K.A., et al., "Knocking Down Barriers: Advances in siRNA Delivery," Nature Reviews: Drug Discovery 8(2):129-138, Feb. 2009.
Yezhelyev, M.V., et al., "Proton-Sponge-Coated Quantum Dots for siRNA Delivery and Intracellular Imaging," Journal of the American Cancer Society (JACS) 130(28):9006-9012, Jul. 2008.
Yong, K.-T., "Mn-Doped Near-Infrared Quantum Dots as Multimodal Targeted Probes for Pancreatic Cancer Imaging," Nanotechnology 20(1):015102, Jan. 2009, 10 pages.
Zhou, L., et al., "Facile One-Pot Synthesis of Iron Oxide Nanoparticles Cross-Linked Magnetic Poly(vinyl alcohol) Gel Beads for Drug Delivery," Applied Materials & Interfaces 4(1):192-199, Jan. 2012.
Chauhan, A., et al., "The Taming of the Cell Penetrating Domain of the HIV Tat: Myths and Realities," Journal of Controlled Release 117(2):148-162, Feb. 2007.
Hong, H., et al., "In Vivo Imaging of RNA Interference," Journal of Nuclear Medicine 51(2):169-172, Feb. 2010.
Howard, K.A., "Delivery of RNA Interference Therapeutics Using Polycation-Based Nanoparticles," Advanced Drug Delivery Reviews 61(9):710-720, Jul. 2009.
Mitchell, D.J., et al., "Polyarginine Enters More Efficiently Than Other Polycationic Homopolymers," Journal of Peptide Research 56(5):318-325, Nov. 2000.

\* cited by examiner

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: Synthetic

<400> SEQUENCE: 1
gcaagcugac ccugaaguuc uu                    22

<210> SEQ ID NO 2
<211> LENGTH: 22
<212> TYPE: RNA
<213> ORGANISM: Artificial Sequence
<220> FEATURE:
<223> OTHER INFORMATION: Synthetic

<400> SEQUENCE: 2
gaacuucagg gucagcuugc uu                    22

POLYARGININE-COATED MAGNETIC NANOVECTOR AND METHODS OF USE THEREOF

CROSS-REFERENCE TO RELATED APPLICATION

This application is a division of U.S. patent application Ser. No. 13/893,137, filed May 13, 2013, which claims the benefit of U.S. Patent Application No. 61/646,101, filed May 11, 2012, each of which is expressly incorporated herein by reference in its entirety.

STATEMENT OF GOVERNMENT LICENSE RIGHTS

This invention was made with government support under Grant Nos. RO1CA134213 and RO1EB006043 awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 41027_SEQ_FINAL.txt. The text file is 631 Bytes; was created on May 7, 2013; and is being submitted via EFS-Web with the filing of the specification.

BACKGROUND OF THE INVENTION

Small interfering RNAs (siRNAs) can silence gene expression in a highly specific manner for treating genetic disorders, signifying a new approach in cancer therapy through the regulation of aberrant gene expression inherent to cancer. However, the physicochemical characteristics of siRNA (e.g., high molecular weight, anionic charge, and hydrophilic character) hinder its passive diffusion across cell membranes precluding any therapeutic function. Furthermore, siRNA molecules are highly vulnerable to degradation. Thus, for effective siRNA delivery, siRNA carriers are needed to protect siRNA, facilitate cellular entry, avoid endosomal compartmentalization, and promote localization in the cytoplasm where the siRNA cargo can be recognized by the RNA-induced silencing complex (RISC). Inorganic nanoparticles (NPs) designed for this application are propitious as they can be engineered for simultaneous diagnostics and therapeutics (theranostics). Currently, many NP core material formulations such as gold, silica, semiconductors, and metal oxides are being evaluated as siRNA carriers (nanovectors). Among them superparamagnetic iron oxide NPs possess superior physicochemical and biological properties ideal for in vivo magnetic resonance imaging (MRI) and drug delivery.

The success of nanovectors relies on the apt design and integration of coatings that ensure biocompatibility and stability in a biologic milieu and proper intracellular trafficking. To date, most nanovectors developed for gene delivery applications are coated with cationic synthetic polymers (e.g., polyethylenimine (PEI), poly amidoamines (PAMAM)) or lipids. A common characteristic among these carriers is their high cationic charge density at physiological pH, which contributes to both the complex formation with anionic siRNA and interaction with the negatively charged cell membrane. This interaction with cell membranes typically leads to the endocytosis of the nanovector, entrapping the nanovector within cellular endosomal vesicles. Within the cellular endosomes the amino groups of cationic polymers function as proton sponges causing the swelling and eventual rupture of the endosome releasing the nanovector into the cytoplasm, a process known as endosomal escape. However, the high cationic charge density of these synthetic polymers also renders them highly cytotoxic.

Despite the advances in the development of siRNA carriers, a need exists for an siRNA carrier that is effective intracellular delivery of siRNA and that provides a safer alternative to the highly cationic nanovectors. The present invention seeks to fulfill this need and provides further related advantages.

SUMMARY OF THE INVENTION

In one aspect, the present invention provides a nanoparticle having a polyarginine coating. In certain embodiments, the nanoparticle has a core that includes a material that imparts magnetic resonance imaging activity to the particle. The nanoparticle can further include one or more of a therapeutic agent that can be delivered by the particle, a targeting agent to target the nanoparticle to a site of interest, and a diagnostic agent that allows for imaging of the particle.

In one embodiment, the nanoparticle, comprises:

(a) a core having a surface and comprising a core material; and (b) a polyarginine coating covalently coupled to the surface of the core.

In certain embodiments, the nanoparticle further comprises a therapeutic agent covalently coupled to the nanoparticle. In other embodiments, the nanoparticle further comprises a targeting agent covalently coupled to the nanoparticle. In further embodiments, the nanoparticle further comprises a therapeutic agent and a targeting agent covalently coupled to the nanoparticle.

Suitable therapeutic agents include small organic molecules, peptides, aptamers, proteins, and nucleic acids. In certain embodiments, the therapeutic agent is an RNA (e.g., siRNA) or a DNA. In certain embodiments, the therapeutic agent is covalently coupled to the coating is coupled through a cleavable linkage.

Suitable targeting agents include small organic molecules, peptides, aptamers, proteins, and nucleic acids.

In certain embodiments, the nanoparticles of the invention further comprise a diagnostic agent. Representative diagnostic agents include optical agents, such as fluorescent agents.

In certain embodiments, the nanoparticle's core material is a magnetic material.

In another aspect, the invention provides a composition comprising a nanoparticle of the invention and a carrier suitable for administration to a warm-blooded subject.

In a further aspect of the invention, a method for introducing a nanovector into a cell via transcytosis is provided. In one embodiment, the method includes contacting a cell with a nanoparticle of the invention.

In another aspect of the invention, a method for silencing or reducing the expression level of a gene is provided. In one embodiment, the method includes contacting a cell of interest with a nanoparticle of the invention.

In another aspect, the invention provides a method for treating a tissue. In one embodiment, the method includes contacting a tissue of interest with a nanoparticle of the invention.

In a further aspect of the invention, a method for silencing or reducing the expression level of a gene is provided. In one embodiment, the method includes contacting a cell of interest with a nanoparticle of the invention.

In another aspect, the invention provides a method for detecting cells or tissues by magnetic resonance imaging. In one embodiment, the method includes:

(a) contacting cells or tissues of interest with a nanoparticle of the invention; and (b) measuring the level of binding of the nanoparticle, wherein an elevated level of binding, relative to normal cells or tissues, is indicative of binding to the cells or tissues of interest.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

FIG. 1A is a schematic illustration of a representative amidated PEG-passivated iron oxide nanoparticle (NP) useful for making representative transfection vectors of the invention. FIG. 1B illustrates the chemical structures and the pKa's of cationic polymers pLys, pArg, and PEI used to functionalize the NP. FIG. 1C illustrates the covalent coupling of the cationic polymer to NP. to provide the cationic polymer coated nanoparticle. FIG. 1D illustrates the coupling of the fluorophore-modified siRNA to the cationic polymer coated nanoparticle to provide a representative magnetic nanovector of the invention.

FIG. 2A compares the spectra of NP, PEI, and NP-PEI. FIG. 2B compares the spectra of NP, pLys, and NP-pLys. FIG. 2C compares the spectra NP, pArg, and NP-pArg. All samples were analyzed in $D_2O$.

FIG. 3A compares gel retardation assay results for representative evaluating covalent attachment of siRNA to NPs under normal electrophoresis conditions (Normal Gel) and under heparin treatment (Heparin Gel) to disrupt electrostatic interactions between cationic NPs and anionic siRNA. FIG. 3B compares Z-average hydrodynamic sizes of representative nanovectors before and after siRNA attachment. FIG. 3C compares zeta potentials of representative nanovectors before and after siRNA attachment. FIG. 3D compares TEM images of representative nanovectors at two magnifications (scale bars correspond to 10 nm).

FIG. 4A compares the titration curves for representative nanovectors. FIG. 4B compares the titration curves for the corresponding cationic polymers.

FIG. 5A compares R2 maps of gel phantoms containing representative nanovectors at different concentrations (mM). FIG. 5B compares R2 relaxivity of representative nanovectors as a function of Fe concentration were used to determine relaxivities, which yielded relaxivity values of 78.2 $mM^{-1}S^{-1}$ for NP-PEG-siRNA, 103.7 $mM^{-1}S^{-1}$ for NP-pArg-siRNA, 131.8 $mM^{-1}S^{-1}$ for NP-pLys-siRNA, and 113.6 $mM^{-1}S^{-1}$ for NP-PEI-siRNA.

FIG. 8A illustrates internalization of nanovectors. FIG. 8B illustrates intracellular localization of nanovectors. Scale bars represent 250 nm.

DETAILED DESCRIPTION OF THE INVENTION

The present invention provides a nanoparticle having a polyarginine coating. In certain embodiments, the nanoparticle has a core that includes a material that imparts magnetic resonance imaging activity to the particle. The nanoparticle can further include one or more of a therapeutic agent that can be delivered by the particle, a targeting agent to target the nanoparticle to a site of interest, and a diagnostic agent that allows for imaging of the particle. The therapeutic, targeting, and diagnostic agents can be covalently coupled to the nanoparticle. Methods for making and using the nanoparticles are also provided.

Nanoparticle Having Polyarginine Coating

In one aspect, the invention provides a multifunctional nanoparticle having a polyarginine (pArg) coating. In one embodiment, the nanoparticle comprises (a) a core having a surface and comprising a core material and (b) a polyarginine coating covalently coupled to the surface of the core.

As used herein, the phrase "core having a surface and comprising a core material" refers to a solid nanoparticle. The nanoparticle core is not hollow (e.g., not a solid shell encapsulating a void). The core material can impart functional properties to the nanoparticle (e.g., magnetic properties). The core material is not a polymeric material (e.g., the nanoparticle is not a polymer nanoparticle or a polymeric nanosphere). As used herein the term "polymeric material"

refers to an organic polymer material (e.g., poly(glycidyl methacrylate), poly(styrene), poly(alkylacrylate)). The core's surface defines the core's outermost surface. In the practice of the invention, the core's surface is chemically modified to have a coating thereon. In certain embodiments, the nanoparticle core is a solid core comprising a material having magnetic resonance imaging activity (e.g., iron oxide).

The phrase "polyarginine coating covalently coupled to the surface of the core" refers to coating that substantially surrounds the core and that is covalently coupled to the core's surface. The coating can be directly covalently coupled to the core surface or covalently coupled to the core's surface through one or more other materials (e.g., layers intermediate the core surface and polyarginine coating) that are covalently coupled to the core's surface. The term "polyarginine coating" refers to a coating that is prepared by covalently coupling polyarginine to the core's surface or by covalently coupling polyarginine to a material that is covalently coupled to the core's surface. The nature of the covalent coupling of polyarginine to the core's surface to provide the coating is not particularly critical. Polyarginine can be covalently coupled to the surface by any one of a variety of chemistries known to the skilled person.

Figure 1A:
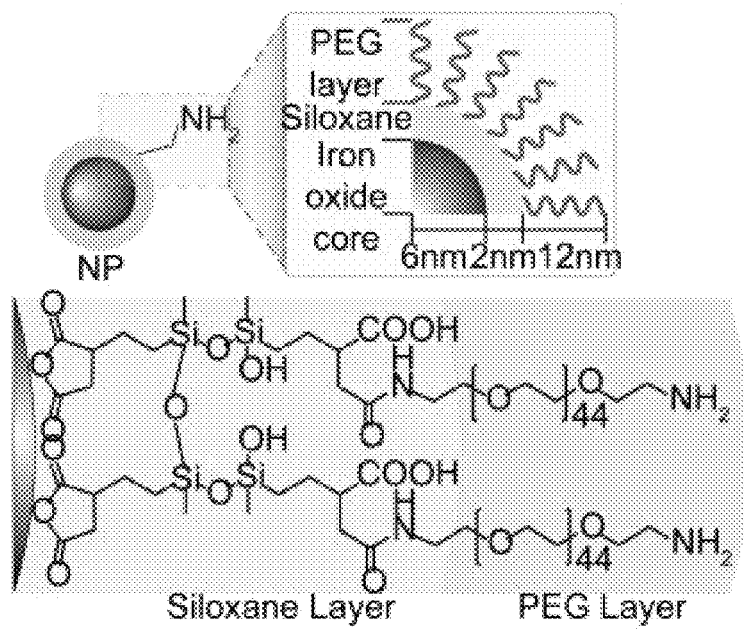
FIGS. 1A-1D illustrate chemical schemes for synthesis of representative magnetic nanovectors of the invention.

In certain embodiments, the nanoparticle of the invention, in addition to the polyarginine coating, includes a poly (alkylene oxide) oligomer coupled to the nanoparticle core through a siloxane layer. In this embodiment, the polyarginine is covalently coupled to the poly(alkylene oxide) oligomer (e.g., poly(ethylene oxide) oligomer). A representative process for covalently coupling polyarginine to a nanoparticle core having poly(ethylene oxide) oligomers coupled thereto is illustrated in FIGS. 1A and 1C. Referring to FIG. 1A, the poly(ethylene oxide) oligomer covalently coupled to the core has a terminal amino (—NH$_2$) group that is functionalized to provide a reactive group (i.e., iodoacetamide) suitable for reaction with a complementary reactive group (i.e., thiol) introduced into the polyarginine (see FIG. 1C). Reaction provides the nanoparticle having a polyarginine coating. In this embodiment, the nanoparticle comprising a poly(alkylene oxide) oligomer intermediate the core and the polyarginine coating. As illustrated in FIG. 1D, the nanoparticle is further modified to include an siRNA (illustrated as including a fluorescent agent coupled thereto) by further suitable functionalization of the nanoparticle and siRNA. The terminal amino groups of the poly(ethylene oxide) oligomer serve as points for functionalization of the nanoparticle. Polyarginine, therapeutic agents (e.g., siRNA), targeting agents, and diagnostic agents can be covalently coupled to the nanoparticle through these terminal amino groups by a variety of chemistries known to those of skill in the art.

As illustrated in FIG. 1A, in certain embodiments, the poly(alkylene oxide) oligomer is covalently coupled to the core through intermediate siloxane linkages. The siloxane layer forms a coating on the core surface. The siloxane is anchored to the core surface (e.g., oxide surface) by interactions between the core surface and functional groups of the siloxane (i.e., to provide core-siloxane linkages). In this embodiment, amino-functionalized poly(alkylene oxide) oligomer is reacted with a suitably functionalized siloxane layer (e.g., carboxylic acid groups). As shown in FIG. 1A, the siloxane layer is covalently coupled to the nanoparticle core and the amino-functionalized poly(ethylene oxide) is covalently coupled to the siloxane layer by amide linkages.

The representative nanoparticle (NP) illustrated in FIG. 1A that is useful for making the functionalized nanoparticles of the invention has a core having a radius from about 5 to about 20 nm (e.g., about 6 nm), a siloxane layer having a radius from about 1 to about 5 nm (e.g., about 2 nm), and a poly(alkylene oxide) layer having a radius from about 2 to about 15 nm (e.g., about 12 nm). The core of the nanoparticle is relatively small (e.g., 5 to 20 nm; 10-15 nm) and monodispersed.

In certain embodiments, the number of amino groups per nanoparticle prior to reaction to provide the siloxane coated nanoparticle is from about 30 to about 200. In one embodiment the nanoparticle includes about 70 amino groups. The nanoparticles of the invention include from about 0.1 to about 0.8 percent by weight polyarginine per nanoparticle. The weight ratio of nanoparticle to siRNA is from about 5 to about 20 (defined as Fe mass of NP:siRNA mass). In certain embodiments, the polyarginine and the siRNA are coupled to the amino groups provided by the amino-polyethylene oxide (PEG-amino). Targeting and/or diagnostic agents can also be covalently coupled to the nanoparticle through these amino groups.

As described herein, the nanoparticles of the invention advantageously include a polyarginine coating. As noted above, the polyarginine coating is prepared by covalently coupling polyarginine to the nanoparticle core or by covalently coupling polyarginine to a material that is covalently coupled to the core. Suitable polyarginines have a molecular weight from about 2,000 to about 200,000 grams/mole. In certain embodiments, the polyarginine has a molecular weight from about 5,000 to about 100,000 grams/mole. In other embodiments, the polyarginine has a molecular weight from about 10,000 to about 50,000 grams/mole. In further embodiments, the polyarginine has a molecular weight from about 7,500 to about 15,000 grams/mole.

In certain embodiments, in addition to the polyarginine coating, the nanoparticle of the invention includes a poly (ethylene oxide) oligomer coupled to the nanoparticle core through a siloxane layer. Suitable poly(ethylene oxide) oligomers include poly(ethylene oxides) (PEO or PEG) and poly(ethylene oxide) copolymers such as block copolymers that include poly(ethylene oxide) and poly(propylene oxide) (e.g., PEO-PPO and PEO-PPO-PEO). In one embodiment, the poly(ethylene oxide) oligomer is a poly(ethylene oxide). In certain embodiments, poly(ethylene oxide) oligomer has a molecular weight (weight average, Mw) of from about 0.3 to about 40 kDa. In others embodiments, the poly(ethylene oxide) oligomer has a molecular weight of from about 1.0 to about 10 kDa. In certain embodiments, the poly(ethylene oxide) oligomer has a molecular weight of about 10 kDa.

The nanoparticle includes a core material. For magnetic resonance imaging applications, the core material is a material having magnetic resonance imaging activity (e.g., the material is paramagnetic). In certain embodiments, the core material is a magnetic material. In other embodiments, the core material is a semiconductor material. Representative core materials include ferrous oxide, ferric oxide, silicon oxide, polycrystalline silicon oxide, silicon nitride, aluminum oxide, germanium oxide, zinc selenide, tin dioxide, titanium, titanium dioxide, nickel titanium, indium tin oxide, gadolinium oxide, stainless steel, gold, and mixtures thereof.

The particle of the invention has nanoscale dimensions. Suitable particles have a physical size less than about 50 nm. In certain embodiments, the nanoparticles have a physical size from about 10 to about 50 nm. In other embodiments, the nanoparticles have a physical size from about 10 to about 30 nm. As used herein, the term "physical size" refers to the overall diameter of the nanoparticle, including core (as determined by TEM) and coating thickness. Suitable particles have a mean core size of from about 2 to about 25 nm. In certain embodiments, the nanoparticles have a mean core size of about 7 nm. As used herein, the term "mean core size" refers to the core size determined by TEM. Suitable particles have a hydrodynamic size less than about 150 nm. In certain embodiments, the nanoparticles have a hydrodynamic size from about 20 to about 150 nm. In certain embodiments, the nanoparticles have a hydrodynamic size of about 33 nm. As used herein, the term "hydrodynamic size" refers the radius of a hard sphere that diffuses at the same rate as the particle under examination as measured by DLS. The hydrodynamic radius is calculated using the particle diffusion coefficient and the Stokes-Einstein equation given below, where k is the Boltzmann constant, T is the temperature, and η is the dispersant viscosity:

$$R_H = \frac{kT}{6\pi\eta D}.$$

A single exponential or Cumulant fit of the correlation curve is the fitting procedure recommended by the International Standards Organization (ISO). The hydrodynamic size extracted using this method is an intensity weighted average called the Z average.

The nanoparticles of the invention include the polyarginine-coated nanoparticles described above that further include one or more other agents. Thus, in other embodiments, the nanoparticles of the invention further include one or more of a therapeutic agent that can be delivered by the particle, a targeting agent to target the nanoparticle to a site of interest, or a diagnostic agent that allows for imaging of the particle. The therapeutic, targeting, and diagnostic agents can be covalently coupled to the nanoparticle.

Therapeutic Agents.

Therapeutic agents effectively delivered by the nanoparticles of the invention include small organic molecules, peptides, aptamers, proteins, and nucleic acids. In certain embodiments, the therapeutic agent is an RNA or a DNA (e.g., an siRNA).

Suitable therapeutic agents include conventional therapeutic agents, such as small molecules; biotherapeutic agents, such as peptides, proteins, and nucleic acids (e.g., DNA, RNA, cDNA, siRNA); and cytotoxic agents, such as alkylating agents, purine antagonists, pyrimidine antagonists, plant alkaloids, intercalating antibiotics, antitumor antibiotics (e.g., trastuzumab), binding epidermal growth factor receptors (tyrosine-kinase inhibitors), aromatase inhibitors, anti-metabolites (e.g., folic acid analogs, methotrexate, 5-fluoruracil), mitotic inhibitors (e.g., taxol, paclitaxel, docetaxel), growth factor inhibitors, cell cycle inhibitors, enzymes, topoisomerase inhibitors, biological response modifiers, anti-hormones, anti-androgens, and various cytokines for immunotherapy. Representative cytotoxic agents include BCNU, cisplatin, gemcitabine, hydroxyurea, paclitaxel, temozomide, topotecan, fluorouracil, vincristine, vinblastine, procarbazine, dacarbazine, altretamine, cisplatin, methotrexate, mercaptopurine, thioguanine, fludarabine phosphate, cladribine, pentostatin, fluorouracil, cytarabine, azacitidine, vinblastine, vincristine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminoglutethimide, anastrozole, amsacrine, asparaginase, mitoxantrone, mitotane, and amifostine.

Suitable therapeutic drugs include siRNAs and antitumor tumor drugs than function in cytoplasm.

In one embodiment, the invention provides a nanoparticle, comprising:

(a) a core comprising a magnetic material and having a surface;

(b) a polyarginine coating covalently coupled to the surface; and (c) a therapeutic agent.

For this embodiment, suitable therapeutic agents are as described above.

For embodiments of the invention that include therapeutic agents, the therapeutic agent can be covalently coupled to the nanoparticle or non-covalently (e.g., ionic) associated with the nanoparticle. For therapeutic agent delivery, the therapeutic agent can be covalently linked (e.g., through a cleavable linkage) or physically adsorbed to (e.g., electrostatic or van der Waals interactions) to the nanoparticle, or embedded within the nanoparticle's coating.

In certain embodiments, the therapeutic agent is covalently coupled to the nanoparticle through a cleavable linkage. Suitable cleavable linkages include linkages cleavable under acidic conditions such as in the acidic microenvironment of cancer cell (e.g., pH less than physiological pH, from about 4.0 to about 6.8. Representative cleavable linkages include acetal, hydrazone, orthoester, and thioester linkages.

For embodiments of the nanoparticle attached with a therapeutic agent (e.g., siRNA), this combination of the nanoparticle and with a therapeutic agent is a nanovector.

Targeting Agents.

Suitable targeting agents include compounds and molecules that direct the nanoparticle to the site of interest. Suitable targeting agents include tumor targeting agents. Representative targeting agents include small molecules, peptides, proteins, aptamers, and nucleic acids. Representative small molecule targeting agents include folic acid and methotrexate (folate receptors), non-peptidic RGD mimetics, vitamins, and hormones. Representative peptide targeting agents include RGD (avβ3 integrin), chlorotoxin (MMP2), and VHPNKK (endothelial vascular adhesion molecules). Representative protein targeting agents include antibodies against the surface receptors of tumor cells, such as monoclonal antibody A7 (colorectal carcinoma), herceptin (Her2/ner), rituxan (CD20 antigen), and ligands such as annexin V (phosphatidylserine) and transferrin (transferrin receptor). Representative aptamer targeting agents include A10 RNA apatamer (prostate-specific membrane antigen) and Thrm-A and Thrm-B DNA aptamers (human alpha-thrombin protein). Targets for the agents noted above are in parentheses. Representative nucleic acid targeting agents include DNAs (e.g., cDNA) and RNAs (e.g., siRNA).

In one embodiment, the invention provides a nanoparticle, comprising:

(a) a core comprising a magnetic material and having a surface;

(b) a polyarginine coating covalently coupled to the surface; and (c) a targeting agent.

In another embodiment, the invention provides a nanoparticle, comprising:

(a) a core comprising a magnetic material and having a surface;

(b) a polyarginine coating covalently coupled to the surface;

(c) a targeting agent; and (d) a therapeutic agent.

For these embodiments, suitable targeting agents and therapeutic agents are as described above.

Diagnostic Agents.

Suitable diagnostic agents include optical agents, such as fluorescent agents that emit light in the visible and near-infrared (e.g., fluorescein and cyanine derivatives). Representative fluorescent agents include fluorescein, OREGON GREEN 488, ALEXA FLUOR 555, ALEXA FLUOR 647, ALEXA FLUOR 680, Cy5, Cy5.5, and Cy7.

In one embodiment, the invention provides a nanoparticle, comprising:
(a) a core comprising a magnetic material and having a surface;
(b) a polyarginine coating covalently coupled to the surface; and
(c) a diagnostic agent.

In another embodiment, the invention provides a nanoparticle, comprising:
(a) a core comprising a magnetic material and having a surface;
(b) a polyarginine coating covalently coupled to the surface;
(c) a diagnostic agent; and
(d) a therapeutic agent.

In a further embodiment, the invention provides a nanoparticle, comprising:
(a) a core comprising a magnetic material and having a surface;
(b) a polyarginine coating covalently coupled to the surface;
(c) a diagnostic agent;
(d) a targeting agent; and
(e) a therapeutic agent.

For these embodiments, suitable diagnostic agents, therapeutic agents, and targeting agents are as described above.

The preparation of representative nanoparticles of the invention is described in Example 1 and illustrated schematically in FIGS. 1A-1D. A schematic illustration of a representative nanoparticle of the invention including a therapeutic agent (e.g., siRNA) and a fluorescent agent (e.g., DY547) is shown in FIG. 1D.

In another aspect of the invention, a composition is provided that includes a nanoparticle of the invention and a carrier suitable for administration to a warm-blooded subject (e.g., a human subject). Suitable carriers include those suitable for intravenous injection (e.g., saline or dextrose).

Methods for Using Nanoparticle Having Polyarginine Coating

In other aspects, the invention provides methods for using the nanoparticles of the invention.

In certain embodiments, the invention provides methods for introducing a material (e.g., therapeutic and/or diagnostic agent) to a cell. In other embodiments, the invention provides imaging methods such as magnetic resonance imaging when the core has magnetic resonance activity, and optical imaging when the nanoparticle includes a fluorescent agent. As noted above, the nanoparticles of the invention can also be used for drug delivery when the nanoparticle includes a therapeutic agent. For nanoparticles of the invention that include targeting agents, imaging of and drug delivery to target sites of interest are provided.

In one embodiment, the invention provides a method for introducing a nanovector into a cell via transcytosis. In the method, a cell is contacted with a nanovector made with a nanoparticle of the invention. As noted herein, the nanovector made of the nanoparticle of the invention and a therapeutic agent advantageously utilizes transcytosis rather than endocytosis for cellular transport. The ability to use a cell transcytosis mechanism renders the nanoparticle of the invention particularly well suited for intracellular delivery of the cargo (e.g., siRNA).

In another embodiment, the invention provides a method for silencing or reducing the expression level of a gene. In the method, a cell of interest is contacted with a nanoparticle of the invention in which the nanoparticle comprises a vector (i.e., suitable siRNA) effective to silence or reduce the expression level of the particular gene.

In a further embodiment, the invention provides a method for detecting (or imaging) cells or tissues by magnetic resonance imaging, comprising:
(a) contacting cells or tissues of interest with a nanoparticle of the invention having affinity and specificity for the cells or tissues of interest, wherein the nanoparticle comprises
(i) a core comprising a magnetic material and having a surface,
(ii) a polyarginine coating covalently coupled to the surface, and
(iii) a targeting agent, wherein the targeting agent has an affinity and specificity to the cells or tissues of interest; and
(b) measuring the level of binding of the nanoparticle to the cells or tissues of interest, wherein an elevated level of binding, relative to normal cells or tissues, is indicative of binding to the cells or tissues of interest.

In the method, the level of binding is measured by magnetic resonance imaging techniques. In a further embodiment of the above method, the nanoparticle further includes a fluorescent agent. In this embodiment, the level of binding can be measured by magnetic resonance and/or fluorescence imaging techniques. The methods are applicable to detecting or imaging cells or tissues in vitro. The methods are also applicable to detecting or imaging cells or tissues in vivo. In this embodiment, the nanoparticles are administered to a subject (e.g., warm-blooded animal) by, for example, intravenous injection.

In another embodiment, the invention provides a method for treating a tissue, comprising contacting a tissue of interest with a nanoparticle of the invention having affinity and specificity for the tissue of interest, wherein the nanoparticle comprises
(a) a core comprising a core material and having a surface,
(b) a polyarginine coating covalently coupled to the surface, and
(c) a targeting agent, wherein the targeting agent has an affinity and specificity to the cells or tissues of interest.

In a further embodiment of the above method, the nanoparticle further comprises a therapeutic agent. In this embodiment, the therapeutic agent can be covalently linked (e.g., through a cleavable linkage) or physically adsorbed to (e.g., electrostatic or van der Waals interactions) the nanoparticle, or embedded within the nanoparticle's coating. The methods are applicable to treating tissues in vitro. The methods are also applicable to treating tissues in vivo. In this embodiment, the nanoparticles are administered to a subject (e.g., warm-blooded animal) by, for example, intravenous injection.

The following is a description of specific nanovectors of the invention and methods of their use.

Magnetic nanoparticles (MNPs) coated with pArg and functionalized with siRNA and their gene-silencing efficiency in tumor cell lines of the brain, breast, and prostate were evaluated. MNPs coated with polylysine (pLys) or PEI were also prepared for comparison. pLys is another commonly used cationic polypeptide to complex siRNA and deliver siRNA to cytoplasm of cells via endocytosis and endosomal escape.

Nanovector Synthesis

Figure 1B:
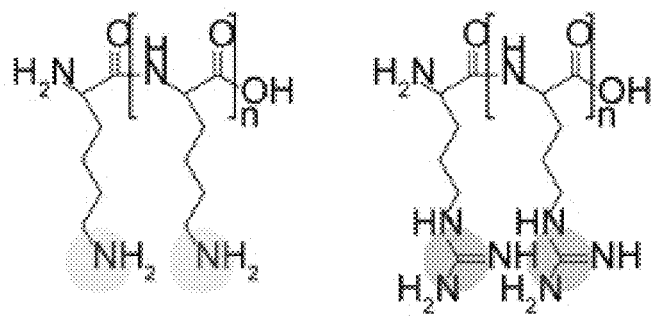
Figure 1B:
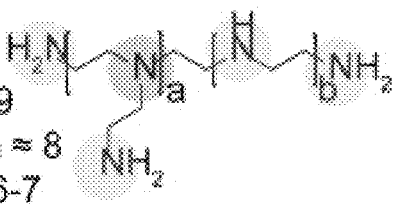
Figure 1C:
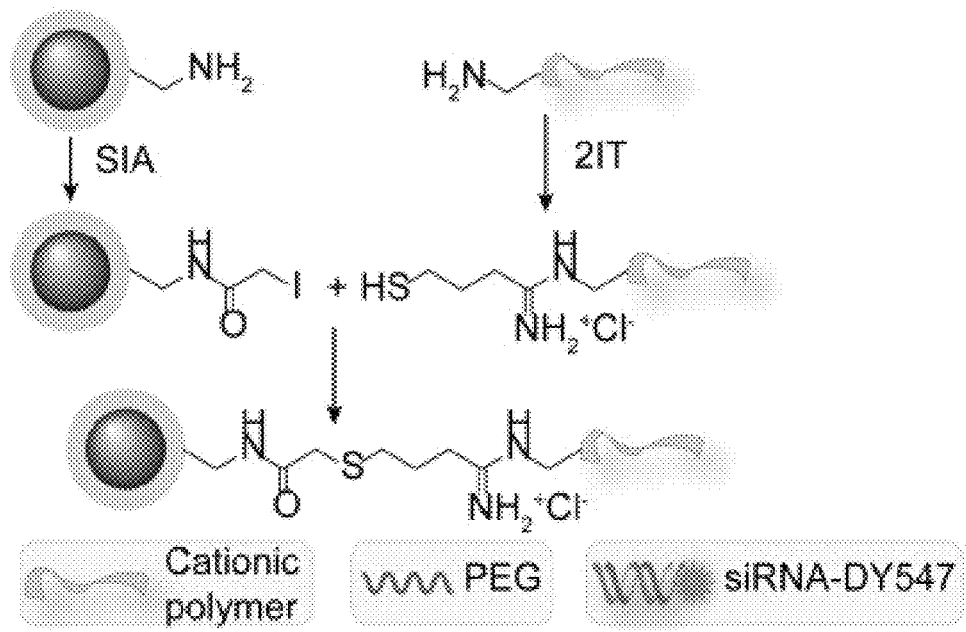
Figure 1D:
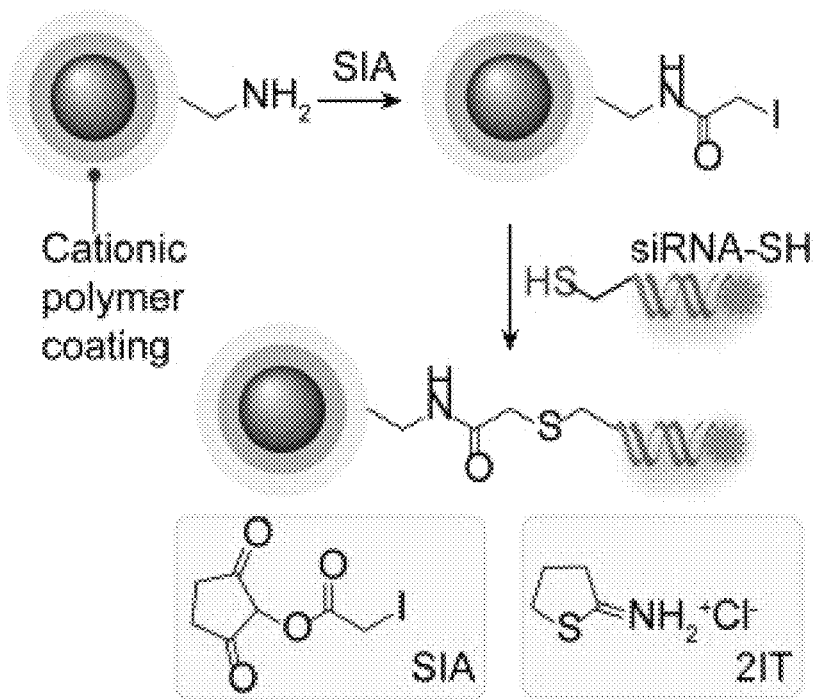

FIGS. 1A-1D illustrates the fabrication scheme a representative nanoparticle of the invention involving the covalent attachment of cationic polymers and siRNA to the amine-functionalized MNPs. The MNP consists of a 10-12 nm iron oxide core coated with siloxane to which a 44-mer of PEG-amine is anchored (FIG. 1A). The MNP was then modified with 10-kDa cationic polymers (pLys, pArg, or PEI) to produce NP-pLys, NP-pArg and NP-PEI using the conjugation scheme in FIG. 1C. The chemical structures of the cationic polymers are shown in FIG. 1B.

To assess the gene delivery efficacy, Cy5 fluorescently labeled, thiol modified siRNA (21 base-pairs, 5.7 nm length) designed to silence green fluorescence protein (GFP) transgene expression was covalently attached to the functional amine groups on the surface of NP-pLys, NP-pArg and NP-PEI using the heterobifunctional linker SIA (FIG. 1D) to form NP-pLys-siRNA, NP-pArg-siRNA and NP-PEI-siRNA.

This non-labile covalent attachment of siRNA to a nanocarrier is preferable for in vivo applications because it ensures that the siRNA-carrier construct will remain intact during blood circulation. Furthermore, this conjugation strategy does not compromise the knockdown efficiency of the siRNA. To favor thioether bond formation over electrostatic binding of the negatively charged siRNA with cationic NP, the SIA reaction was performed in a high ionic strength buffer.

Nanovector Physicochemical Characterization

Figure 2A:
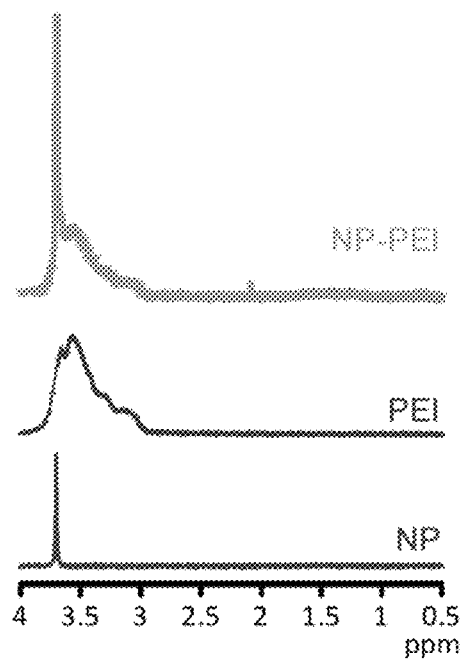
FIGS. 2A-2C illustrate the proton NMR spectra of representative nanovectors verifying cation polymer coating attachment.
Figure 2B:
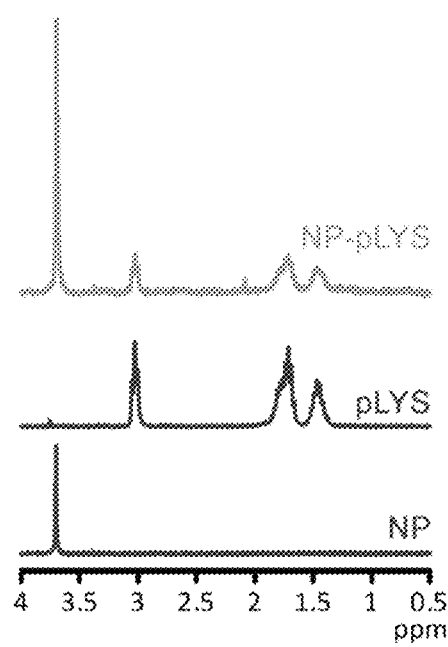
Figure 2C:
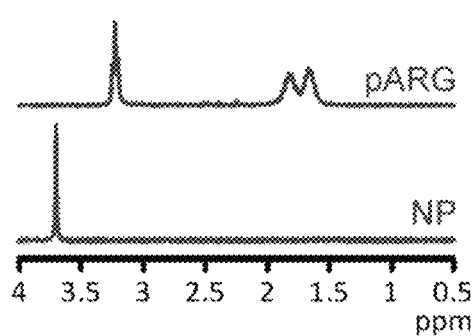
Figure 3A:
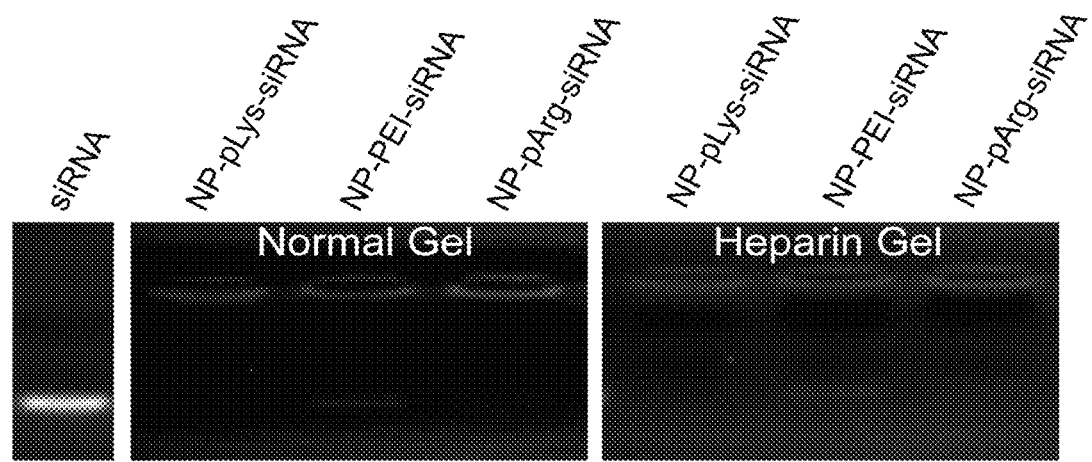
FIGS. 3A-3D provides the characterization of representative nanovectors.

The successful immobilization of cationic polymers onto NP was verified using proton NMR ($^1$H-NMR). Spectra from base MNPs, relevant constituent polymers, and the three different nanovector formulations confirm the successful immobilization of their expected polymer coatings FIGS. 2A and 2B. PEG on NP was identified at 3.7 ppm corresponding to the protons of the ethylene unit. PEI was identified at 3.75-3 ppm corresponding to the protons of its ethylene units. pLys was identified at 3, 1.75, and 1.45 ppm corresponding to the protons of the $\epsilon$, $\delta$ and $\beta$, and $\gamma$ carbons of the lysine side chain. pArg was identified at 3.25, 1.8, and 1.6 ppm corresponding to the protons of the $\delta$, $\beta$, and $\gamma$ carbons of the arginine side chain, respectively.

siRNA loading onto the nanovector was assessed using gel retardation assays where NP bound siRNA would not migrate down the gel. NP-pLys-siRNA, NP-PEI-siRNA and NP-pArg-siRNA were prepared at 20:1 nanoparticle:siRNA weight ratios (Fe mass of NP:siRNA mass). Without purification, the reaction products were loaded into agarose gels and unbound siRNA (bottom of gel) was separated from MNP-bound siRNA through electrophoresis. Each NP formulation showed complete binding of siRNA as no unbound siRNA was observed in the gels (FIG. 3A). A similar migration profile is demonstrated in the heparin treated samples (FIG. 3A), which disrupts electrostatic interactions, confirming successful covalent attachment of siRNA to MNP for all three nanovector formulations.

Figure 3B:
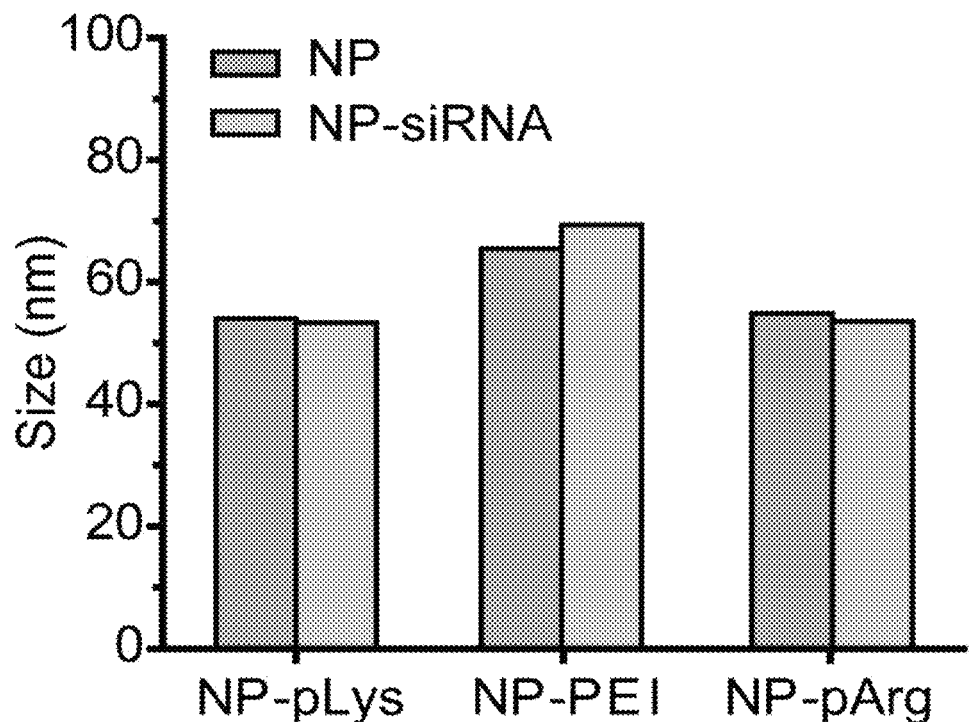

The hydrodynamic size of each nanovector formulation before and after siRNA loading was measured by dynamic light scattering (DLS) (FIG. 3B). Z-average diameters of the nanovectors were 53.4 nm for NP-pLys-siRNA, 69.4 nm for NP-PEI-siRNA and 53.5 nm for NP-pArg-siRNA. No significant change in hydrodynamic size was observed after siRNA attachment to nanovectors, reflecting their stability. Notably, the hydrodynamic size falls within the acceptable size range (5<d<200 nm) that facilitates in vivo navigation and evasion of sequestration by macrophages.

Figure 3C:
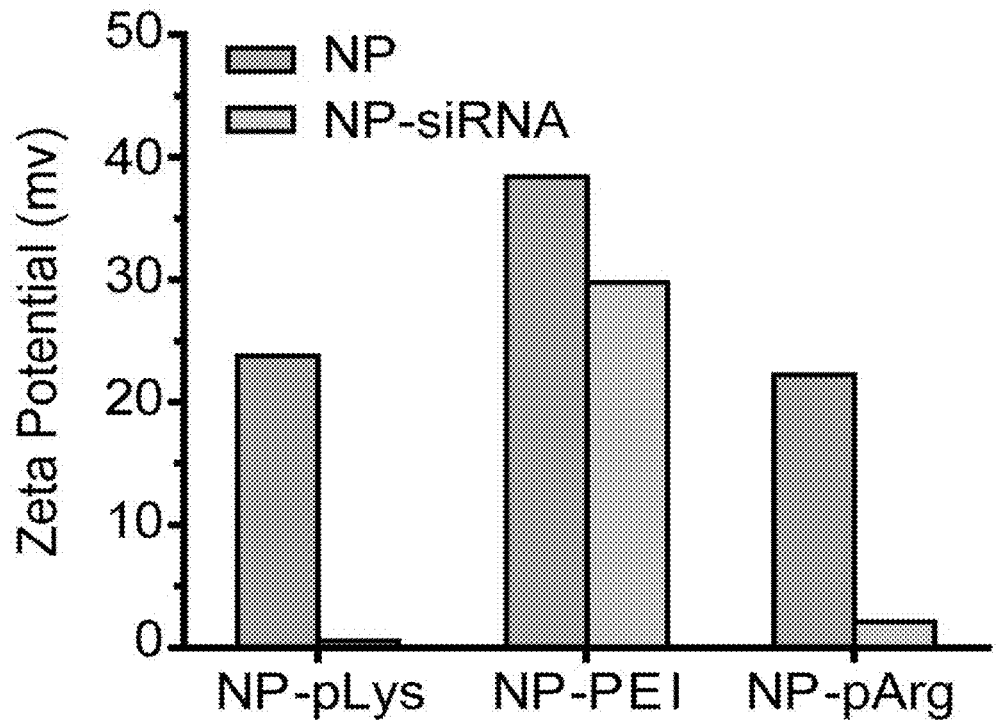
Figure 3D:
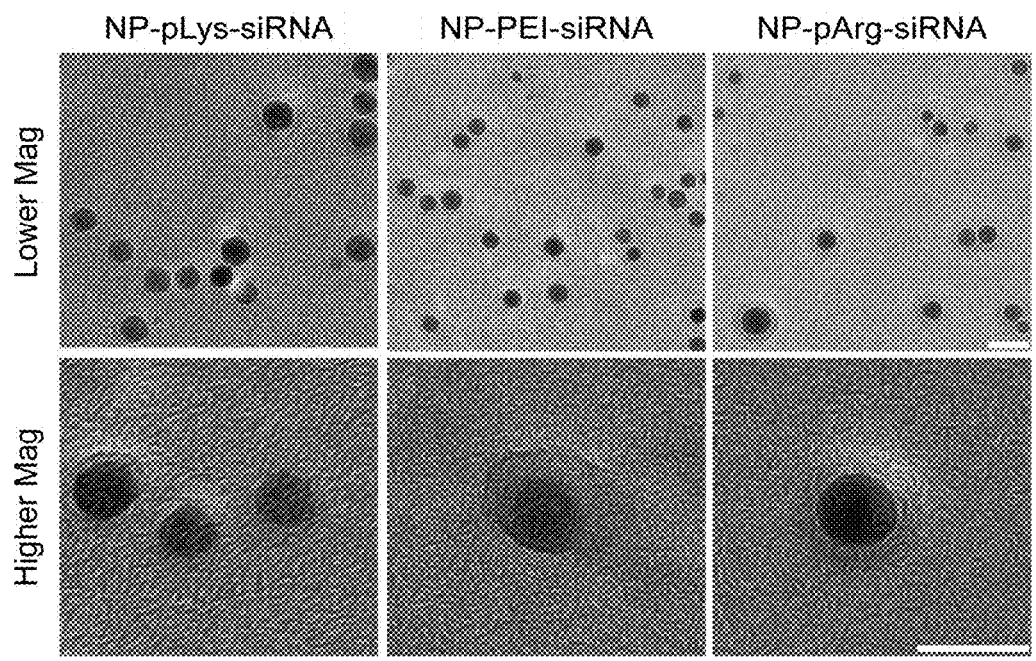
Figure 9:
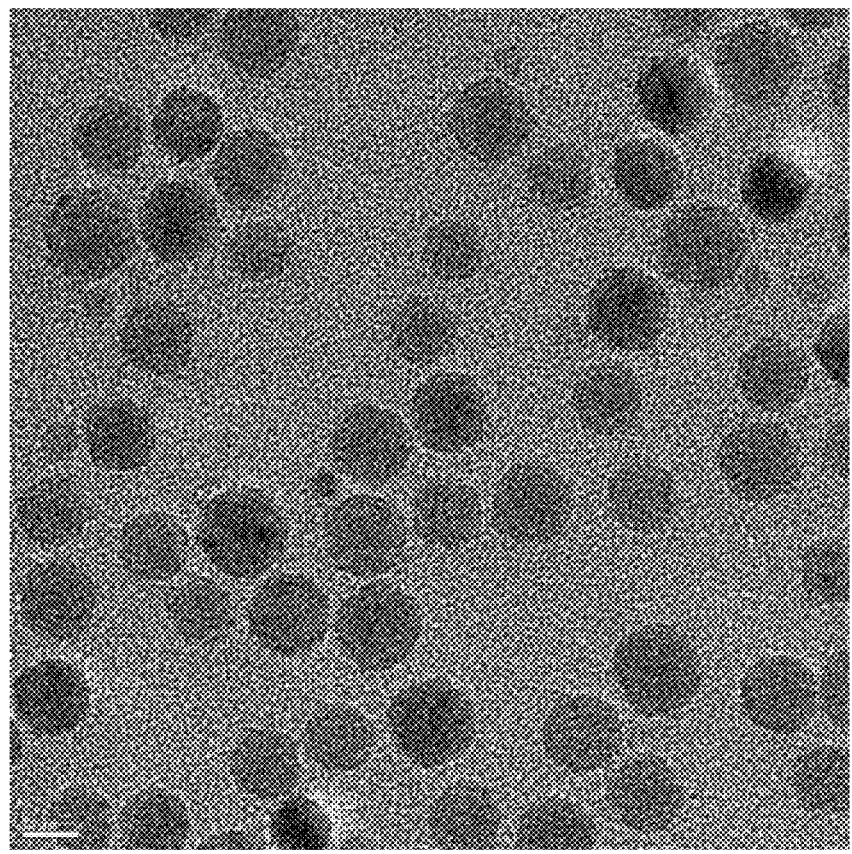
FIG. 9 is a TEM image of NP-PEG-amine (NP) useful for preparing representative nanovectors of the invention. Scale bar corresponds to 10 nm.

TEM images of three nanovector formulations show no signs of aggregation (FIG. 3D, top row). Higher magnification images in FIG. 3D (bottom row) reveal a lower density shell surrounding the MNP cores, which is absent on the base MNPs (FIG. 9). This shell structure further confirms the cationic polymer coating on the MNPs.

The zeta potential of each nanovector formulation was measured at pH 7.4 in 10 mM HEPES buffer by DLS. All three nanovector formulations were highly cationic prior to siRNA attachment, with zeta potentials of 22 mV for NP-pLys, 39 mV for NP-PEI and 21 mV for NP-pArg (FIG. 3C). After siRNA attachment, the zeta potentials of all formulations dropped significantly confirming successful siRNA conjugation. However, NP-PEI-siRNA remained highly cationic (30 mV) while the NP-pLys-siRNA (0.5 mV), and NP-pArg-siRNA (2.5 mV) displayed near-neutral zeta potentials under physiological pH conditions. A neutral NP formulation generally has better biocompatibility and prolonged circulating time in blood than positively charged formulations.

Figure 4A:
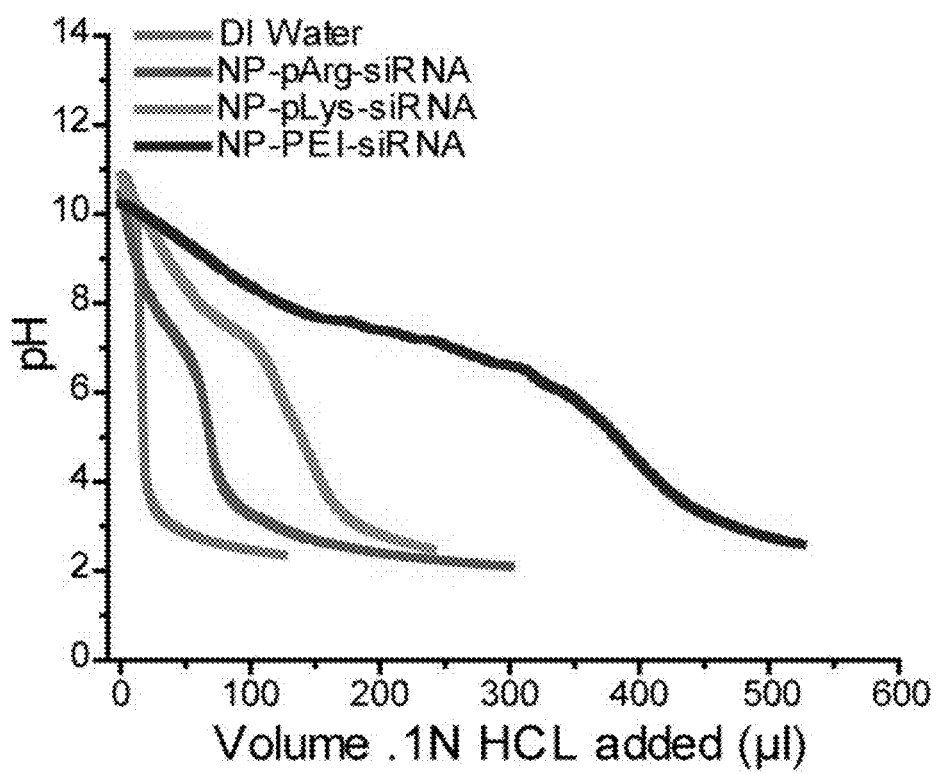
FIGS. 4A and 4B compare titration curves evaluating the buffering capacity (addition of sodium hydroxide) of each nanovector formulation.
Figure 4B:
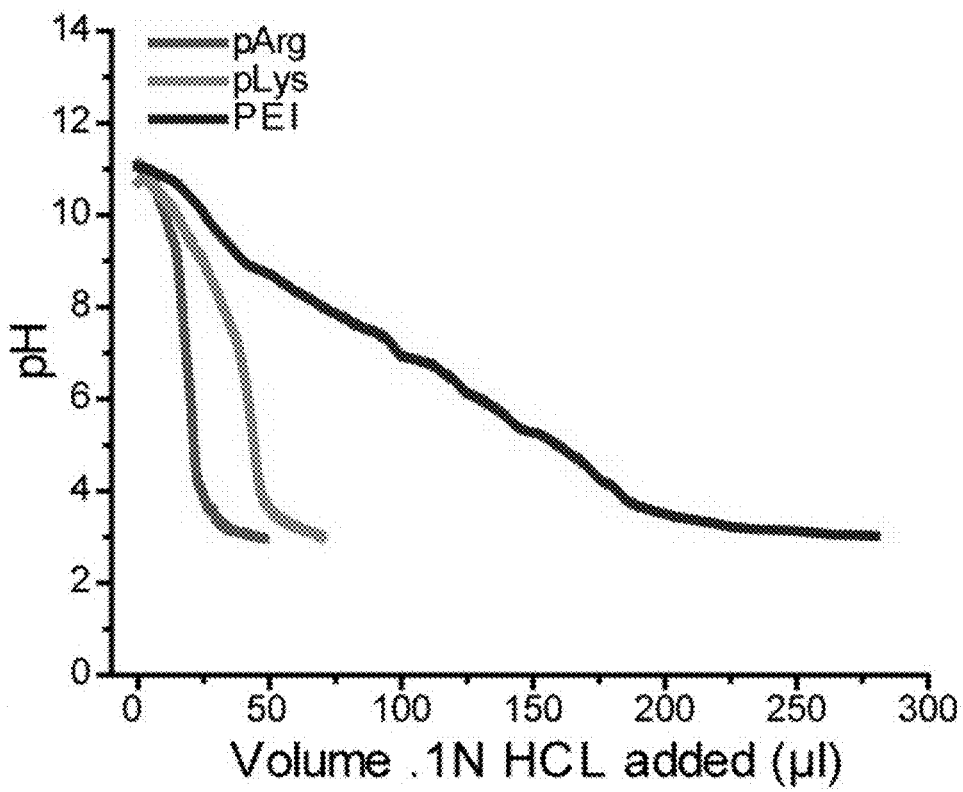

The three various nanovector formulations were similar in sizes, but had different zeta potentials. They differ in composition and abundance of surface amino groups, providing us an opportunity to compare the influence of these key parameters on siRNA delivery and cytotoxicity. The charge and composition of the cationic polymer coating regulates the buffering capacity and proton sponge behavior of the nanovector. To illustrate this, nanovectors were titrated with HCL and the change in pH was monitored. Resistance to pH change indicates an increase in proton absorption of the nanovector. The buffering capacity was seen to increase in the order of NP-pArg-siRNA<NP-pLys-siRNA<NP-PEI-siRNA (FIG. 4A). This trend mirrors the buffering capacities of the coating polymers alone (FIG. 4B), indicating they were not affected by attachment to NPs or to siRNA.

Figure 5A:
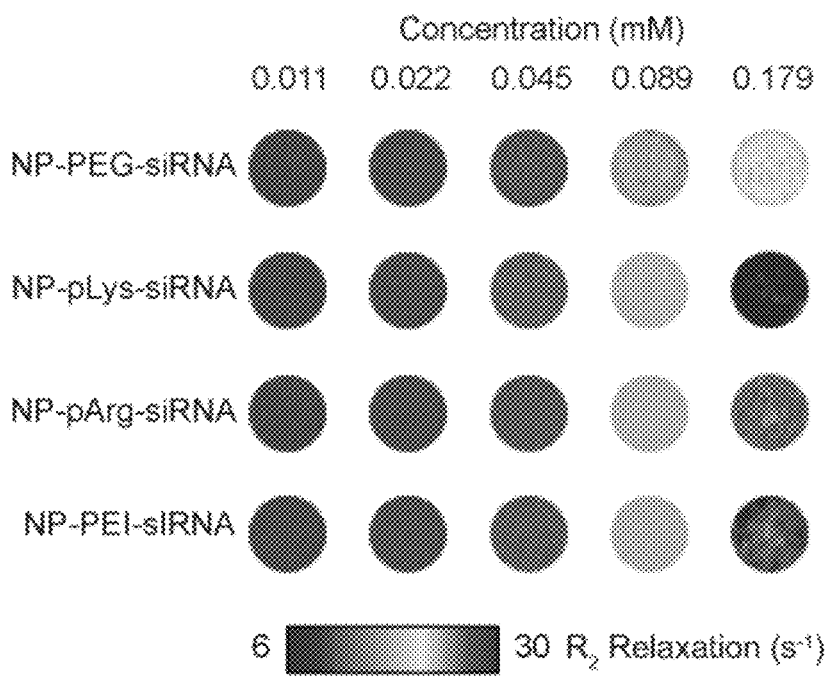
FIGS. 5A and 5B illustrate the magnetic properties of nanovectors.
Figure 5B:
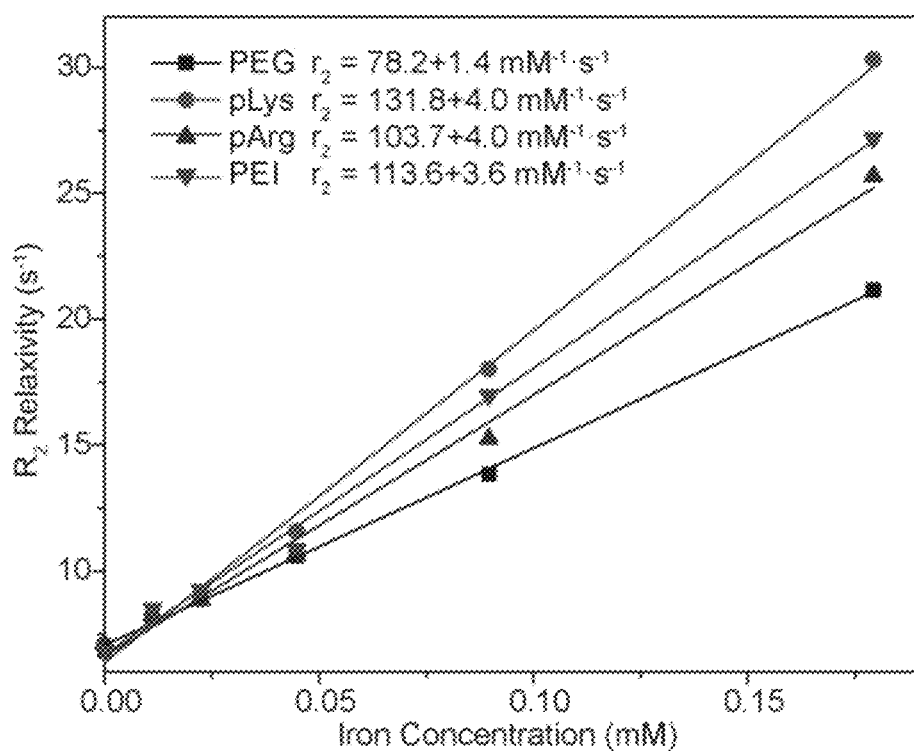

To ensure the shell structure did not compromise the magnetic properties of the nanovectors, their magnetic relaxivities on MRI were evaluated. All nanovector formulations showed higher $R_2$ relaxivities compared to the base NP (FIGS. 5A and 5B), suggesting that the attachment of cationic polymers and siRNA to MNPs did not compromise, but rather, improved the magnetic properties. This improvement is likely due to the improved water absorption at the surface of the core MNP due to the presence of the hydrophilic cationic polymers.

Nanovector Internalization, Gene Knockdown and Monitoring of Toxicity

Figure 6A:
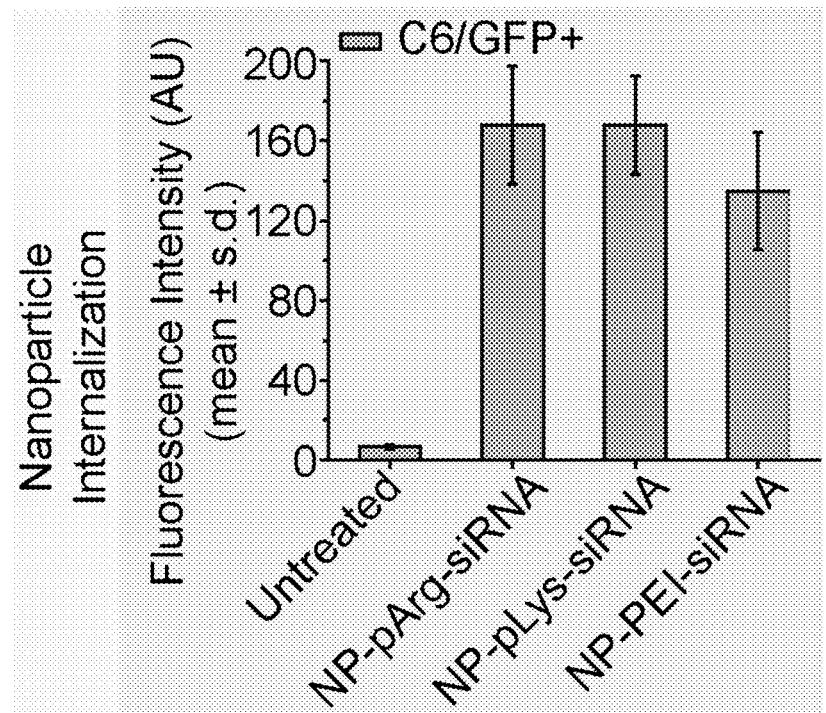
FIGS. 6A-6I compare siRNA delivery, cell viability, and GFP knockdown for representative nanovectors. Relative amount of siRNA delivered to C6/GFP$^+$ (FIG. 6A), MCF7/GFP$^+$ (FIG. 6B), and TC2/GFP$^+$ (FIG. 6C) cells by nanovectors of three different formulations. Influence of nanovector treatments on cell viability of C6/GFP$^+$ (FIG. 6D), MCF7/GFP$^+$ (FIG. 6E), and TC2/GFP$^+$ cells (FIG. 6F) (viability was normalized to untreated cells). Efficiency of nanovector treatments on silencing GFP expression in C6/GFP$^+$ (FIG. 6G), MCF/GFP$^+$ (FIG. 6H), and TC2/GFP$^+$ (FIG. 6I) cells (GFP expression was normalized to untreated cells).
Figure 6B:
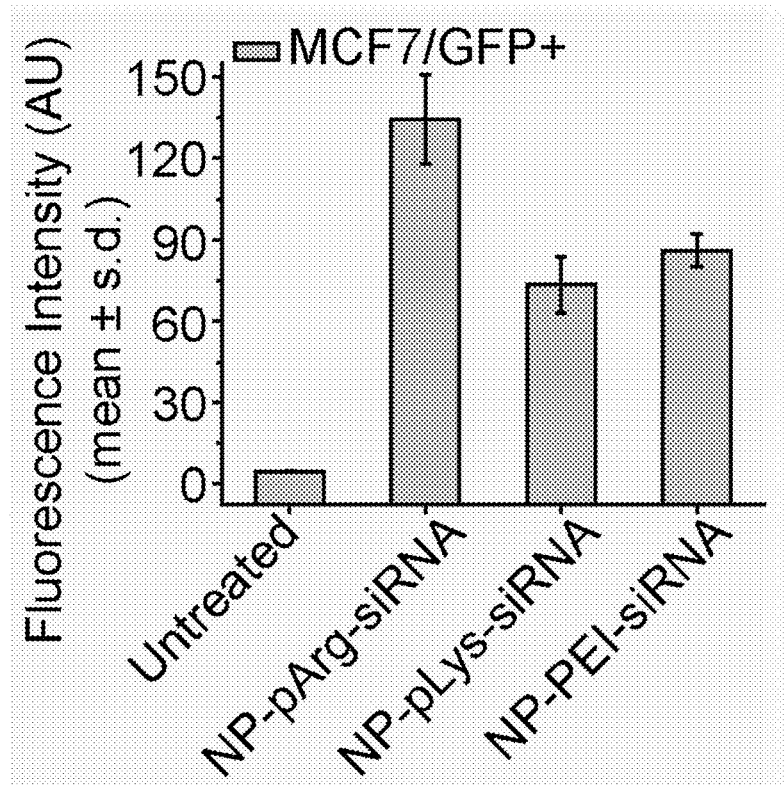
Figure 6C:
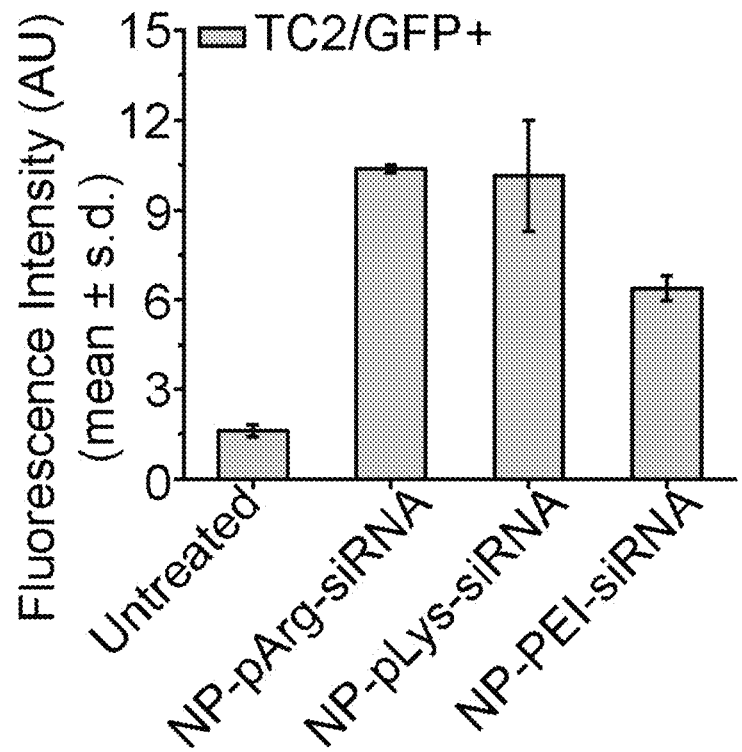

The nanovectors were evaluated in vitro for siRNA delivery and gene silencing in three cancer cell lines (C6/GFP$^+$ brain, MCF7/GFP$^+$ breast, and TC2/GFP$^+$ prostate) that stably express the GFP gene. First, the amount of siRNA delivered to cells by each nanovector formulation was evaluated using the fluorescently labeled siRNA (FIGS. 6A-6C). All three nanovectors delivered similar amounts of siRNA to C6/GFP$^+$ cells (FIG. 6A). Conversely, NP-pArg-siRNA delivered a markedly higher quantity of siRNA to MCF7/GFP$^+$ cells than NP-pLys-siRNA and NP-PEI-siRNA (FIG. 6B). In TC2/GFP$^+$ cells, both NP-pArg-siRNA and NP-pLys-siRNA delivered more siRNA than NP-PEI-siRNA. These data demonstrate that the pArg coating was most broadly effective in facilitating the delivery of siRNA-loaded nanovectors to target cells.

Figure 6D:
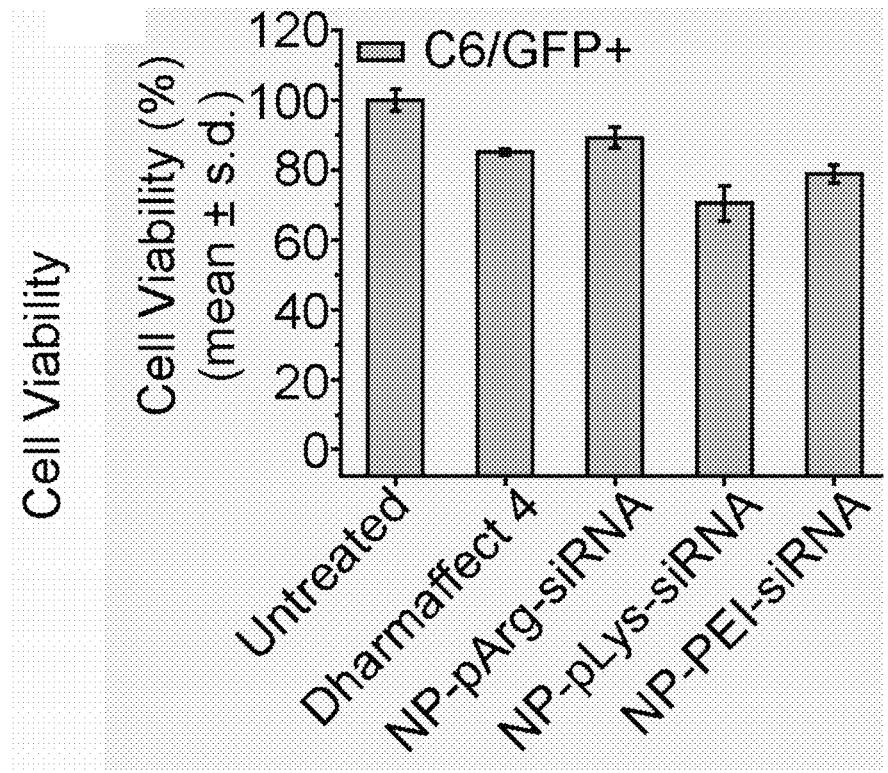
Figure 6E:
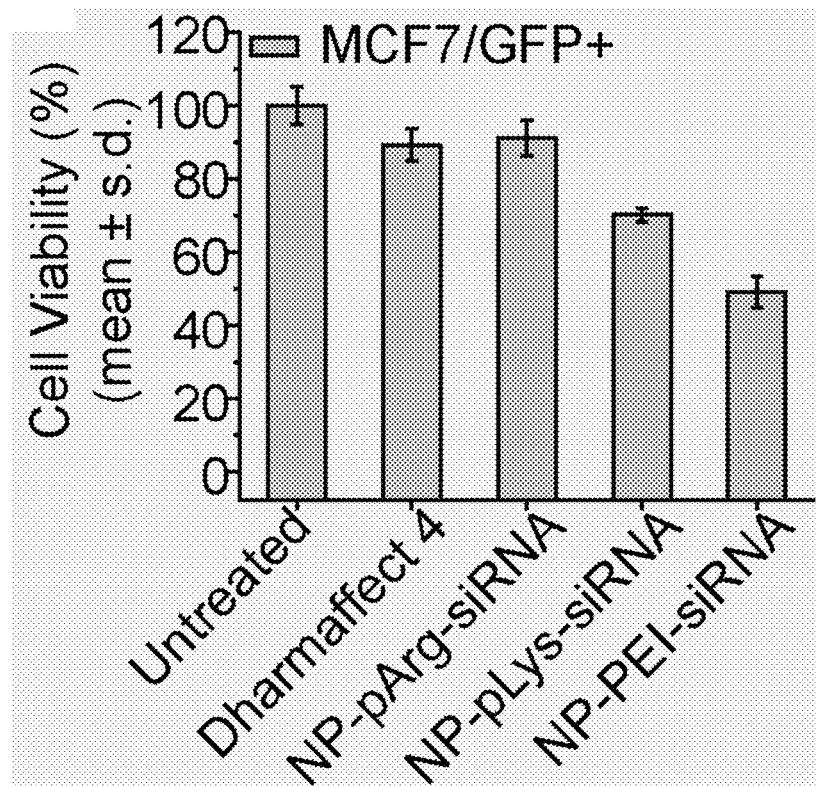
Figure 6F:
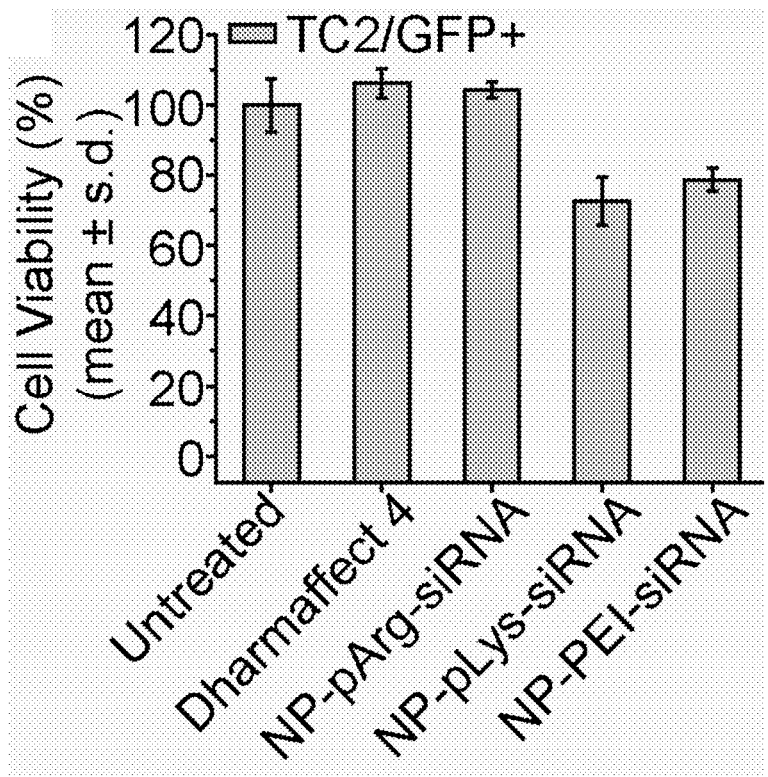

The influence of nanovector treatments on cell viability was evaluated using Alamar blue assays. Cells were treated with each nanovector formulation and a commercial transfection reagent Dharmafect 4 (Dharmacon Inc.) as a reference. The NP-pArg-siRNA treatment was the least toxic to C6/GFP+ cells (90% viability (% V)), with NP-pLys-siRNA (70.6% V) and NP-PEI-siRNA (78.9% V) most toxic (FIG. 6D). A similar trend in viability was observed with MCF7/GFP+ cells (FIG. 6E) where NP-pArg-siRNA treatment produced the least cytotoxicity (91.2% V), similar to Dharmafect 4 treatment (89% V) and much lower than NP-pLys-siRNA (70.2% V) and NP-PEI-siRNA (49% V) treatments. This trend was again observed in TC2/GFP+ cells (FIG. 6F). Both NP-pArg-siRNA (104.3% V) and Dharmafect 4 (92.5% V) treatments were well tolerated, while the NP-pLys-siRNA (77.5% V) and NP-PEI-siRNA (78.7% V) treatments were both moderately toxic.

Figure 6G:
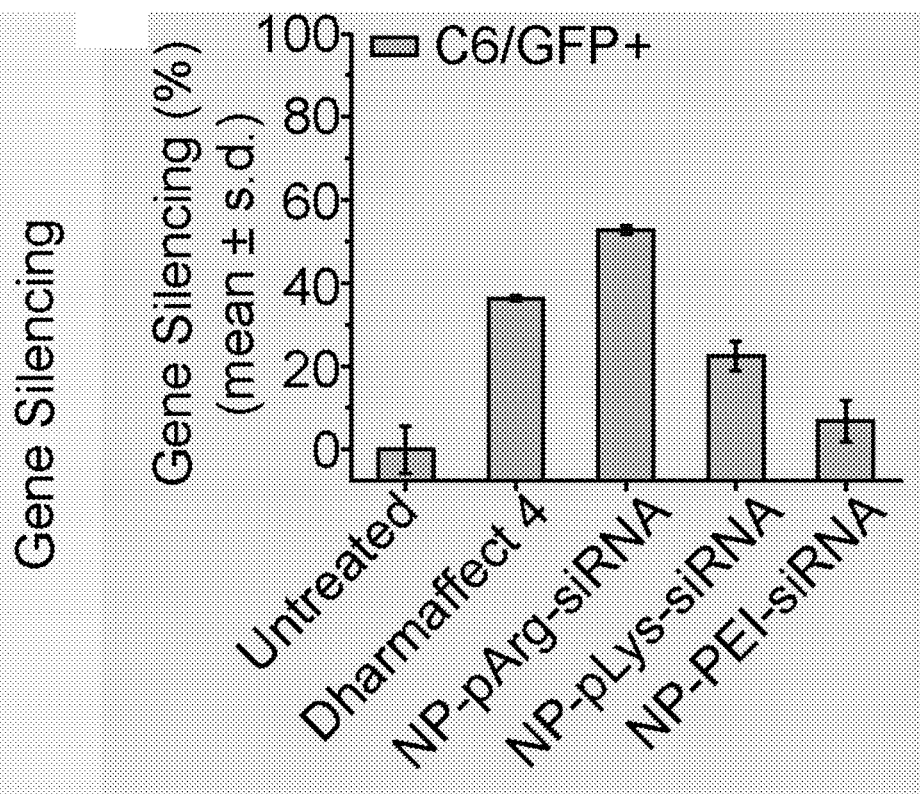
Figure 6H:
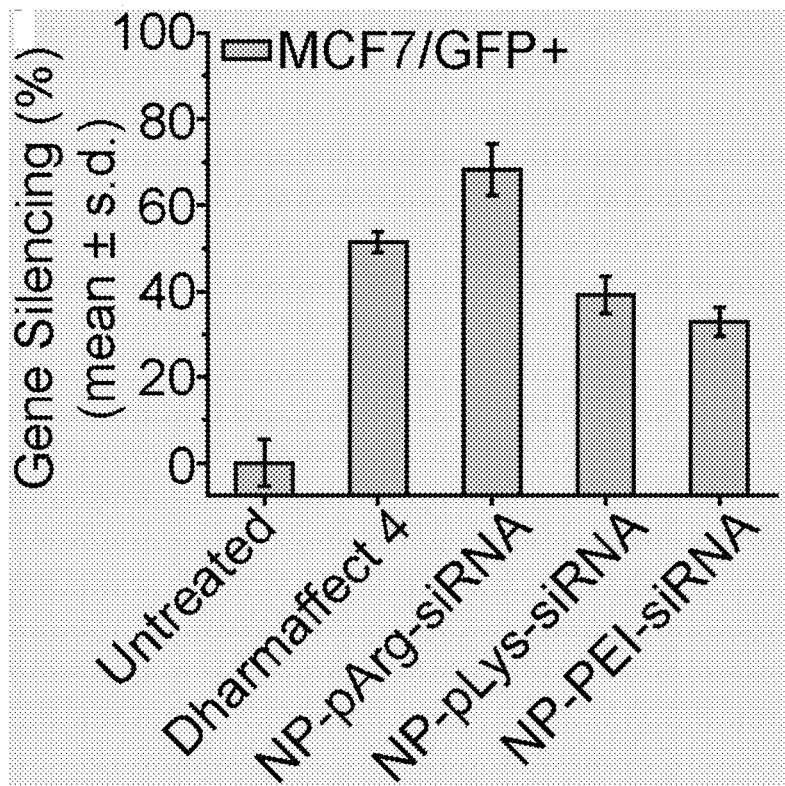
Figure 6I:
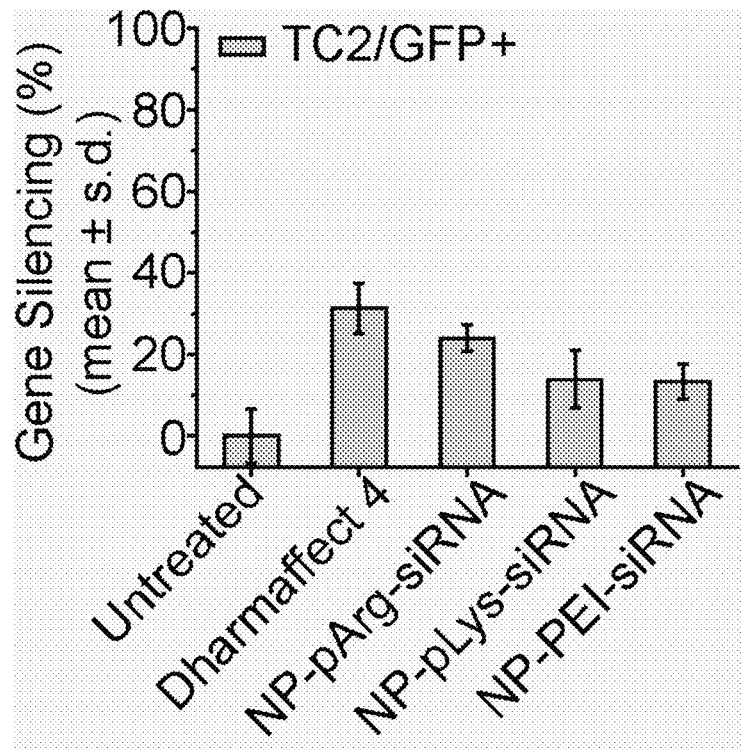

The GFP gene-silencing efficacy of each nanovector formulation was then evaluated (FIGS. 6G-6I). The NP-pArg-siRNA treatment was most effective in gene silencing in C6/GFP+ cells (52.9% GFP knockdown (% GKD)), whereas Dharmafect 4 (36.4% GKD), NP-pLys-siRNA (22.7% GKD) and NP-PEI-siRNA (6.8% GKD) were all significantly less effective (FIG. 6G). A similar trend was observed in MCF7/GFP+ cells (FIG. 6H). NP-pArg-siRNA showed the highest potency for silencing (68.2% GKD), whereas Dharmafect 4 (51.3% GKD), NP-pLys-siRNA (39.1% GKD) and NP-PEI-siRNA (32.8% GKD) treatments were all less effective. In TC2/GFP+ cells it was again observed that NP-pArg-siRNA (24% GKD) was most effective in gene silencing compared to the other two different nanovector formulations, NP-pLys-siRNA (13.9% GKD) and NP-PEI-siRNA (13.4% GKD) (FIG. 6I). In this cell line Dharmafect 4 (31.3% GKD) was slightly more effective than NP-pArg-siRNA.

Figure 7A:
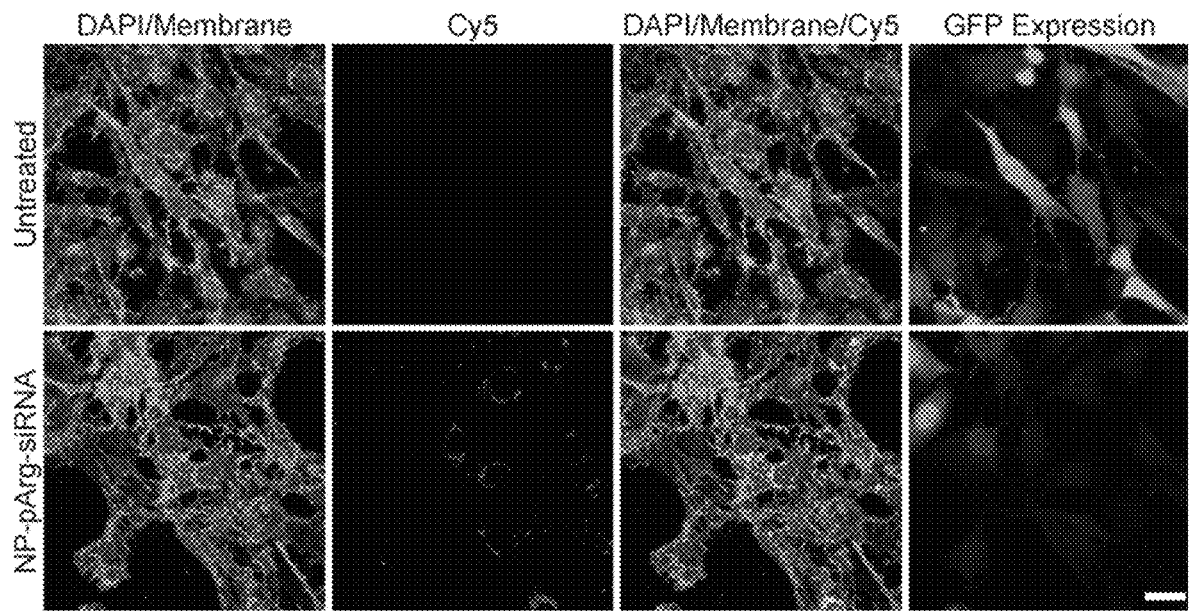
FIGS. 7A-7C are confocal fluorescence microscopy images evaluating siRNA internalization and subsequent GFP knockdown for representative nanovectors. Images were acquired from C6/GFP+ (FIG. 7A), MCF7/GFP+ (FIG. 7B), and TC2/GFP+ (FIG. 7C) cells 48 hours post treatment with NP-pArg-siRNA, with untreated cells as a reference. Scale bar corresponds to 20 μm.
Figure 7B:
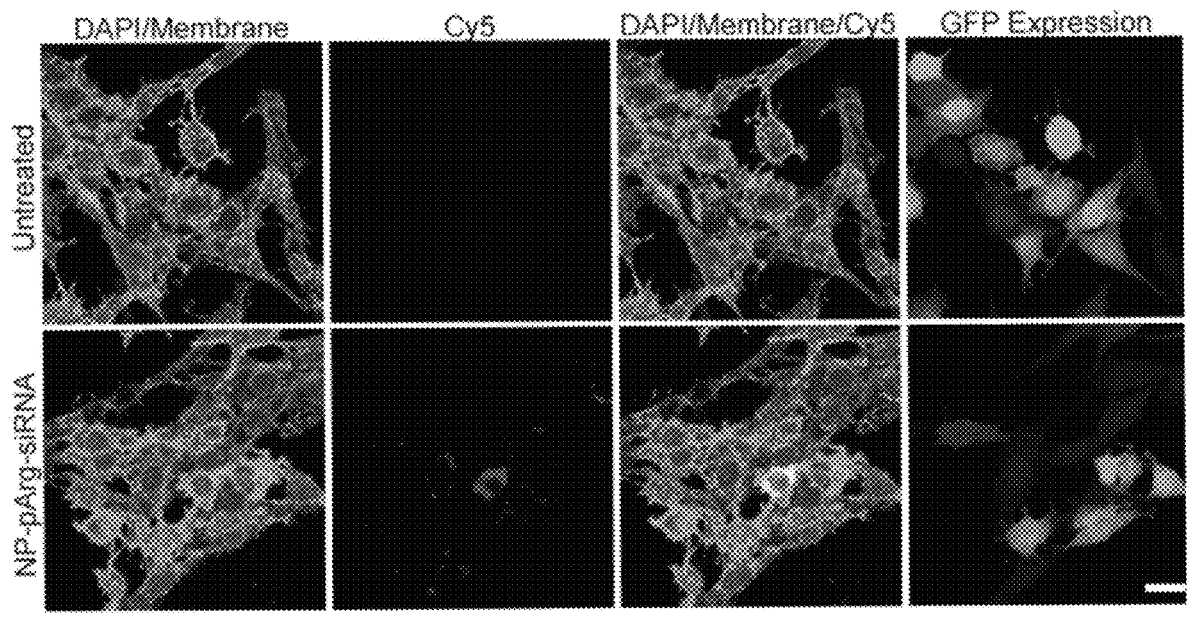
Figure 7C:
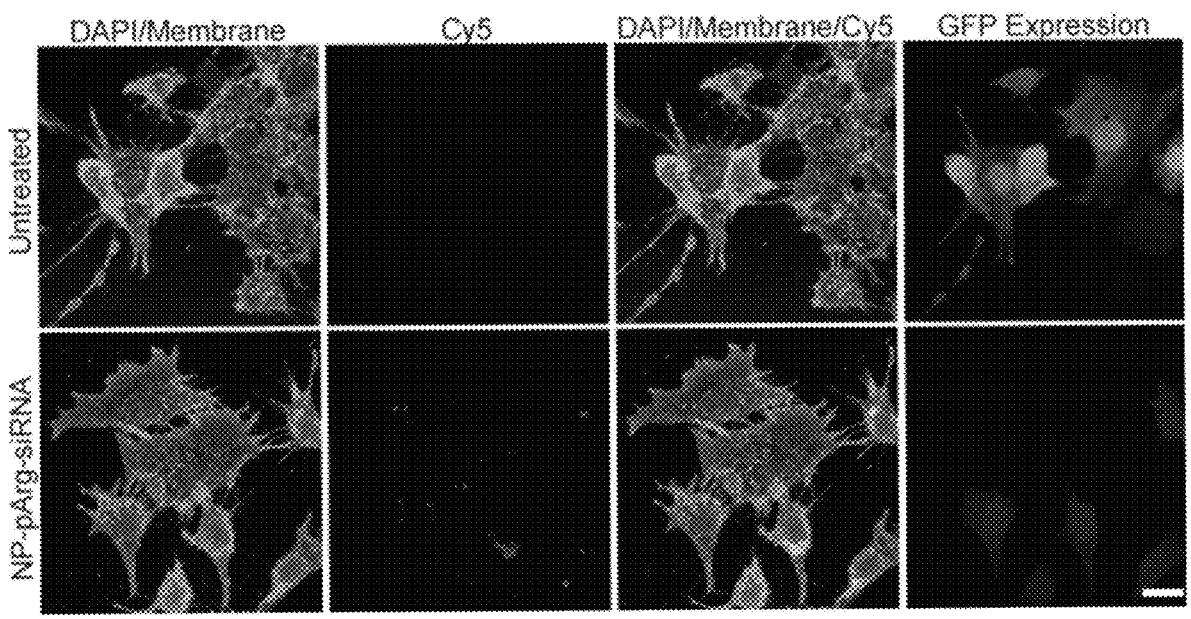

To further confirm the siRNA delivery and gene knockdown achieved by NP-pArg-siRNA to the three types of cells (C6/GFP+, MCF7/GFP+, and TC2/GFP+) confocal fluorescence microscopy was performed. Shown in FIGS. 7A-7C are fluorescence images of untreated and NP-pArg-siRNA treated C6/GFP+ (FIG. 7A), MCF7/GFP+ (FIG. 7B), and TC2/GFP+ (FIG. 7C) cells. In all images cell nuclei were stained with DAPI (blue) and membranes with WGA-647 (green). Treatments with NP-pArg-siRNA were administered as described above at a concentration of 1.2 µg of siRNA/ml. As shown in all three-cell lines tested internalized siRNA (red, second column) can be visualized in cells treated with NP-pArg-siRNA. The overlay images (third column) reveal that the delivered siRNA molecules are predominantly localized in the perinuclear region of cells, the region of cell where siRNA molecules are recognized by the RISC complex. This observation confirms the proper trafficking of siRNA within cells. The GFP expression analysis (light green, fourth column) showed that the NP-pArg-siRNA treatment reduced the GFP expression of cells in all cell lines compared to the untreated cells.

Based on the transfection and cell viability studies, NP-pArg-siRNA has the favorable overall properties as a theranostic agent compared to other nanovector formulations studied. This might be attributed to its neutral zeta potential and limited proton sponge effect, which minimizes the potential deleterious effects caused by non-specific interactions with anionic intracellular components (e.g., mRNA, DNA). The arginine-rich nanoparticle may travel across cell membranes through transcytosis without being trapped in endosome vesicles. NP-pArg-siRNA may be similarly trafficked into cells accounting for its high gene silencing efficiency despite limited proton sponge capacity.

Nanovector Intracellular Trafficking

Figure 8A:
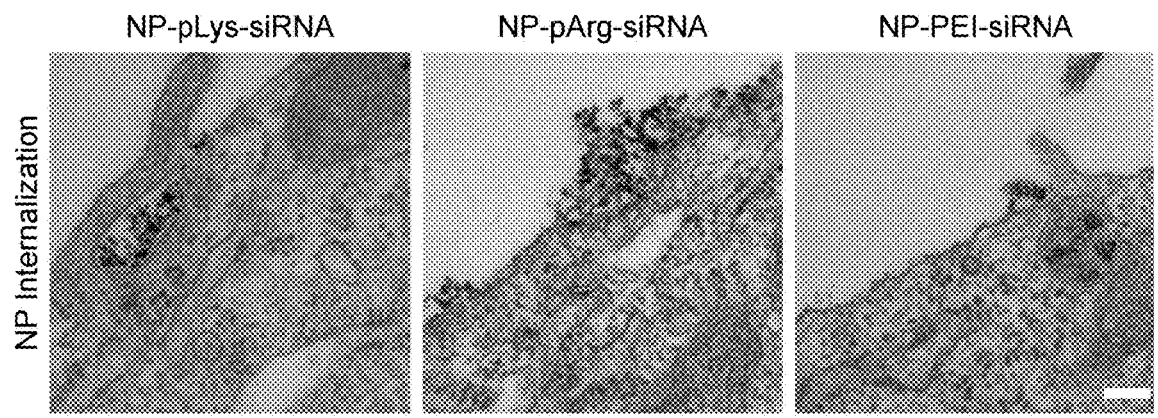
FIGS. 8A and 8B are TEM images of C6/GFP$^+$ cells treated with three representative nanovector formulations (NP-pLys-siRNA, NP-pArg-siRNA, and NP-PEI-siRNA).
Figure 8B:
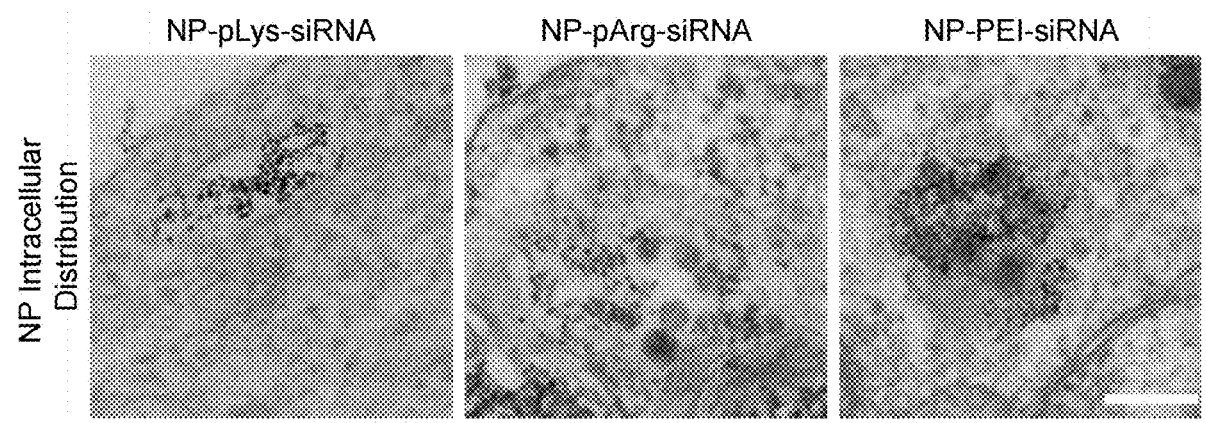

To determine the uptake mechanism of each nanovector formulation, C6/GFP+ cells treated with nanovectors were imaged with TEM (FIGS. 8A and 8B). NP-pLys-siRNA and NP-PEI-siRNA could be observed entering the cell through endocytic pathways, whereas NP-pArg-siRNA appeared to transcytose across the cell membrane in the absence of independent endocytic engulfment (FIG. 8A). Furthermore, once inside the cell NP-pLys-siRNA and NP-PEI-siRNA could be seen escaping endosomal vesicles while NP-pArg-siRNA were free in the cytoplasm with no visible endosomal vesicle (FIG. 8B). These TEM images provide an explanation as to why the NP-pArg-siRNA formulation appeared efficient in inducing gene knockdown (FIGS. 6A-6I), despite its limited buffering capacity (FIG. 4A). The NP-pArg-formulation does not require endosome escape properties owing to its ability to completely bypass the endocytosis pathway. Conversely, the NP-pLys-siRNA and NP-PEI-siRNA formulations must escape endosomal vesicles to localize in the cytoplasm.

The present invention provides nanoparticles useful as siRNA carriers that utilize the polyarginine (pArg) peptide as a coating material. pArg is a naturally occurring, biodegradable polypeptide that offers improved biocompatibility (decreased toxicity) over PEI and PAMAM. Furthermore, because cell transcytosing proteins are known to avoid endosomal compartmentalization and are commonly found with arginine-rich domains, the pArg-coated nanovectors of the invention offer the advantage of transcytosing ability and thus offer more efficient siRNA delivery with greatly improved biocompatibility over NPs coated with synthetic polymers such as PEI.

As used herein, the term "about" refers to values +/−5% of the recited value.

The following is provided for the purpose of illustrating, not limiting, the invention.

The Preparation, Characterization, and Properties of Representative Polyarginine-Coated Nanoparticles (NP-pArg and NP-pArg-siRNA)

The following is a description of the preparation and characterization of representative arginine-coated nanoparticles of the invention (NP-Arg). The preparation and characterization of representative arginine-coated nanoparticles conjugated with siRNA (NP-pArg-siRNA) are also described. The particles and their preparation are schematically illustrated in FIGS. 1A-1D.

All reagents were purchased from Sigma Aldrich (St. Louis, Mo.) unless otherwise specified.

Amine-Terminated PEG-Coated Nanoparticles

Figure 10:
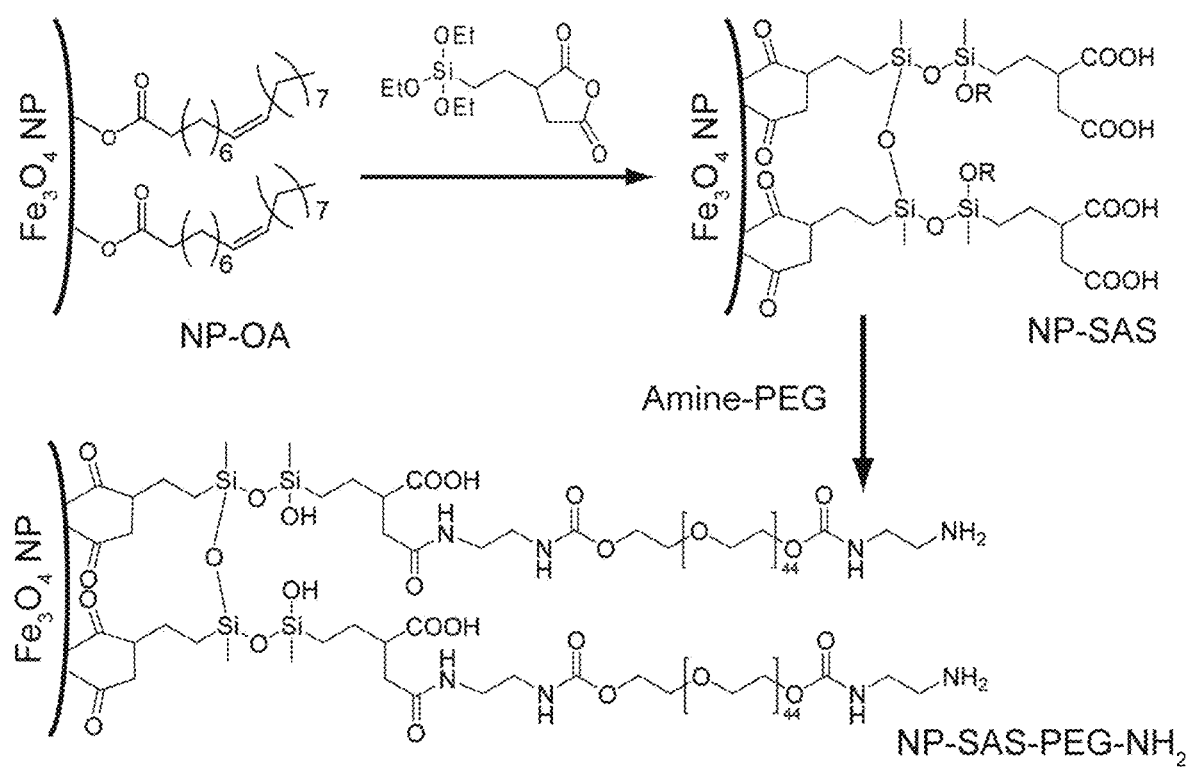
FIG. 10 is a schematic illustration of the preparation a nanoparticle having a modified surface (NP-SAS-PEG-$NH_2$) useful for preparing representative nanovectors of the invention.

Amine-terminated PEG-coated iron oxide nanoparticles (NPs) with a 12 nm core diameter were synthesized as described in Fang C, Bhattarai N, Sun C, Zhang M Q. Functionalized Nanoparticles with Long-Term Stability in Biological Media. Small. 2009; 5:1637-41, expressly incorporated herein by reference in its entirety. A schematic illustration of the preparation of representative amine-terminated PEG-coated iron oxide nanoparticles (NP-SAS-PEG-NH$_2$) is shown in FIG. 10.

Oleic acid-coated nanoparticles (NP-OA) were synthesized via thermal decomposition of iron oleate complex. To render the nanoparticles hydrophilic, the NP-OAs were reacted with triethoxysilylpropylsuccinic anhydride (SAS) to form SAS-coated nanoparticles (NP-SAS) via a ligand-exchange and condensation process. Amine-functionalized PEG was attached to NP-SAS via N,N'-dicyclohexylcarbodiimide (DCC) mediated coupling reaction to yield PEGylated nanoparticles (NP-SAS-PEG-NH$_2$). NP-SAS-PEG-NH$_2$ bears amine groups at the free termini of PEG chains allowing for further conjugation with bioactive molecules or ligands. The PEG coating also serves to prevent nanoparticles from agglomeration and protein adsorption.

Synthesis of NP-SAS-PEG-NH$_2$.

To a 5 ml of toluene solution containing 50 mg (iron content) of NP-OA, 40 mL of acetone was added, and the nanoparticles were collected by centrifugation. The nanoparticles were redispersed in 50 mL anhydrous toluene and transferred to a three-neck flask equipped with a heater. After the system was sealed and purged with nitrogen, 0.15 mL of SAS was injected, and the solution was heated to 100° C. for 12 hours. The nanoparticles were precipitated by the addition of hexane, and collected using a rare earth magnet. The nanoparticles were washed twice with hexane and redispersed in anhydrous tetrahydrofuran (THF). To this solution, 100 mg of H$_2$N-PEG-NH$_2$ and 2.5 mg of N,N'-dicyclohexylcarbodiimide (DCC) were added, and the reaction mixture was sonicated in a sonication bath for 12 hrs at 25° C. The nanoparticles was precipitated by the addition of 200 mL of hexane, and collected using a rare earth magnet. The precipitated nanoparticles were redispersed in 50 mL of anhydrous THF, and 250 mg of PEG-bis(amine) and 12.5 mg of DCC were added. The reaction mixture was kept in a sonication bath for 16 hrs at 25° C. The resulting product was precipitated by the addition of hexane, and collected using a rare earth magnet. After two additional cycles of THF-redispersion and ether-precipitation, the residue solvent was evaporated and the nanoparticles were redispersed in 5 mL PBS. After passing through a 0.2 µm syringe filter, the nanoparticles were purified through gel filtration chromatography by Sephacryl S-200 column. The nanoparticles were stored in 0.1 M sodium bicarbonate buffer (pH 8.5). The concentration of nanoparticles was determined by inductively coupled plasma atomic emission spectroscopy (ICP-AES).

TEM images showed that both NP-OA and NP-SAS-PEG-NH$_2$ were spherical and well dispersed, with a core size of about 12 nm. No aggregation of NP-SAS-PEG-NH$_2$ was observed, indicating that no inter-particle crosslinking occurred during the ligand exchange and PEG modification. Nanoparticle surface modification was confirmed by FTIR and XPS. The IR spectra of oleic acid coated nanoparticles exhibit the characteristic C—H stretch bands of methyl and methylene groups at 2930 and 2849 cm$^{-1}$ and surface-complexed carbonyl stretch peaks at 1553 and 1433 cm$^{-1}$. After the surface modification of nanoparticles with SAS, the Si—O—R vibrational bands, including a broad peak around 1031 cm$^{-1}$ and a minor peak at 1188 cm$^{-1}$, were observed indicating the formation of complex siloxane bonds. The relative intensity of surface-complexed carbonyl bands increased, compared to oleic acid-coated NPs, indicative of successful SAS attachment. The absence of characteristic anhydride peaks at 1850-1800 cm$^{-1}$ and 1790-1740 cm$^{-1}$, suggesting that these groups were either hydrolyzed or bonded to the iron oxide surface. After the surface modification of NP-SAS with amine-functionalized PEG, multiple bands at 1458, 1346, 1244, 1112 and 949 cm$^{-1}$ were observed, corresponding to the different vibrational modes of PEG's C—O—C bonds. The bands at 1642 and 1559 cm$^{-1}$ can be assigned to either primary amine groups or mono-substituted amide, indicating the successful covalent attachment of PEG on the free carboxyl groups of NP-SAS. The number of reactive amine groups on nanoparticles by quantifying pyridine-2-thione following reaction with N-succinimidyl 3-(2-pyridyldithio)propionate (SPDP). The number of amine groups on each nanoparticle was about 70. As the number of amine groups is proportional to the number of PEG chains, this result also suggests the formation of a high density PEG coating on the surface of the nanoparticle.

The hydrodynamic sizes of NP-OA in toluene and NP-SAS-PEG-NH$_2$ in phosphate-buffered saline (PBS) were determined to be 18 nm and 38 nm, respectively, by dynamic light scattering. The size increase (about 20 nm) of the NP-SAS-PEG-NH$_2$ compared to NP-OA can be attributed to the PEG (MW=2,000) coating and the water molecules associated to PEG.

NP-pLys, NP-pArg, and NP-PEI Synthesis

The cationic polymer coated nanoparticles were prepared from amine-terminated PEG-coated iron oxide nanoparticles (NP in FIG. 1A or NP-SAS-PEG-NH$_2$ in FIG. 10). NPs were modified with cationic polymers through the formation of a thioether bond between thiolated polymers and NPs activated with iodoacetyl groups. Specifically, 10.5 mg of NP in 1 mL of thiolation buffer (0.1M sodium bicarbonate, 5 mM EDTA, pH 8.0) was reacted with 10.5 mg succinimidyl iodoacetate (SIA, Molecular Biosciences, Boulder, Colo.) in 112.5 µl DMSO. Concurrently, 15.75 mg of poly-lysine (MW 10,000), poly-arginine (MW 10,000), or PEI (MW 10,000) were dissolved in 1.725 ml thiolation buffer and modified with 26 µl of a 10 mg/ml Traut's reagent (2-iminothiolane, Molecular Biosciences, Boulder, Colo.). All of the reactions were protected from light and ensued under gentle rocking. After 2 hours, excess SIA was removed from NP-SIA using a pre-packed PD-10 desalting column (GE Healthcare, Piscataway, N.J.) equilibrated with thiolation buffer. Upon purification, the NPs were split into three equal volumes, each containing 3.5 mg Fe, and added to the three polymer solutions for reaction. The reaction were protected from light and ensued for 2 hours with gentle rocking and was then stored at 4° C. overnight. The reactants for each reaction were then purified to remove excess polymer using columns packed with S-200 Sephacryl resin (GE Healthcare, Piscataway, N.J.) equilibrated with thiolation buffer.

siRNA Preparation siRNA sequences designed to knockdown GFP expression: 5'-GCAAGCUGACCCUGAAGUUCUU-3'-antisense (SEQ ID NO: 1) and 5'-GAACUUCAGGGUCAGC-UUGCUU-3'-sense (SEQ ID NO: 2) were purchased from Integrated DNA Technologies, Inc. (IDT, San Diego Calif.). These sequences were acquired with protected-thiol modifications on the 5' end of the sense strand and with Cy5 modification on the 5' end of the antisense strand. siRNA sequences were received as single strands and were annealed to their complementary strand in annealing buffer (12 mM potassium chloride, 1.2 mM HEPES, 0.04 mM magnesium chloride, pH 7.5) by incubating at 95° C. for five minutes, then 37° C. for 1 hr, and then stored at −20° C.

NP-pLys-siRNA, NP-pArg-siRNA, and NP-PEI-siRNA Synthesis

NP-pLys, NP-pArg, and NP-PEI were modified with SIA at a 5:1 weight ratio of Fe:SIA. The SIA was dissolved in DMSO such that the final reaction volume was 10% DMSO. The reactions were protected from light and ensued for 2 hours with gentle rocking. Meanwhile, a 57.73 mg/ml TCEP (tris(2-carboxyethyl)phosphine hydrochloride) solution was prepared. The TCEP and GFP siRNA were combined at a 1:1 volume ratio, protected from light, and allowed to react for 1 hr with gentle rocking. The resultant siRNA was purified using a 2 ml Zeba column (Thermo Fisher Scientific, Waltham, Mass.) equilibrated with thiolation buffer. The nanoparticles were purified using pre packed PD-10 columns equilibrated with thiolation buffer. Upon purification, the siRNA was added to each of the three types of NPs at a 20:1 Fe:siRNA weight ratio. The reactions were protected from light and allowed to proceed for 2 hrs with gentle rocking and the resultant nanoparticle:siRNA nanovectors were used without any further purification.

Proton NMR Analysis of Cationic Polymer Attachment to NP

Each NP formulation (50 µg Fe) was dissolved in 50 µL of DCl and diluted to 1 mL in $D_2O$. Similarly, cationic polymers were dissolved in 1 mL $D_2O$ containing 50 µL of DCl. Proton NMR spectra were obtained on a Bruker AVance series spectrometer operating at 300 MHz.

Gel Retardation Assay

Attachment of siRNA to NPs was assessed using gel retardation assays. A 4% low melting point agarose gel was prepared with 0.05 mg/mL ethidium bromide. While maintaining a uniform concentration of siRNA, samples of nanoparticle:siRNA complexes were prepared at a weight ratio of 20:1 (Fe mass of NP:siRNA mass). Samples were either left untreated or treated with heparin (1000 units/ml, 10 mL heparin/mg siRNA), and incubated for 30 min at room temperature to block the electrostatic interaction between the nanoparticles and siRNA. siRNA binding was analyzed by gel electrophoresis at 55 V for 90 min. Images were acquired on a Gel Doc XR (Bio-Rad Laboratories, Hercules, Calif.).

Nanovector Size and Zeta Potential Characterization

Hydrodynamic sizes and zeta potentials of the different nanoparticle formulations were analyzed at 100 µg/mL in 20 mM HEPES buffer (pH 7.4) using a DTS Zetasizer Nano (Malvern Instruments, Worcestershire, UK).

Evaluation of Nanovector Magnetic Properties by MRI

Nanovector formulations were diluted in PBS, and then mixed with 25 µL of 1% agarose and loaded into an agarose gel phantom block. T2 relaxation measurements were performed on a 4.7-T Bruker magnet (Bruker Medical Systems, Karlsruhe, Germany) equipped with Varian Inova spectrometer (Varian, Inc., Palo Alto, Calif.). A 5 cm volume coil and spin-echo imaging sequence were used to acquire T2-weight images. Images were acquired using a repetition time (TR) of 3000 ms and echo times (TE) of 13.6, 20.0, 40.0, 60.0, 90.0 and 120.0 ms. The spatial resolution parameters were: acquisition matrix of 256×128, field-of-view of 35×35 mm, section thickness of 1 mm and two averages. The T2 map was generated by NIH ImageJ (Bethesda, Md.) based on the equation, $SI=A\exp(-TE/T2)+B$, where SI is the signal intensity, TE is the echo time, A is the amplitude, and B is the offset. The R2 map was generated by taking the reciprocal of the T2 map.

Evaluation of Nanovector Buffering Capacity

NP-pLys-siRNA, NP-pArg-siRNA, and NP-PEI-siRNA were desalted using pre-packed PD-10 columns equilibrated with DI water. 1 mg of Fe from each condition was then transferred to a 15 ml Falcon tube and brought to pH 11.0 by addition of 0.1 N NaOH. The final volume for each condition was brought up to 2 ml with pH 11.0 DI water making the Fe concentration 500 µg/ml. The titration was performed with 2 µL additions of 0.1 N HCl.

Cell Culture

C6 rat glioma (ATCC, Manassas, Va.) and MCF7 human adenocarcinoma (ATCC, Manassas, Va.) cells were maintained in Dulbecco's Modified Eagle Medium (DMEM, Invitrogen, Carlsbad, Calif.) supplemented with 10% FBS (Atlanta Biologicals, Lawrenceville, Ga.) and 1% antibiotic-antimycotic (Invitrogen, Carlsbad, Calif.) at 37° C. and 5% $CO_2$. Enhanced green fluorescent protein (EGFP) expressing cells were produced by stably transfecting cells with the pEGFP-N1 vector using the Effectene transfection reagent (Qiagen, Valencia, Calif.) following the manufacturer's protocol. 48 hrs post-transfection, cells were sorted using a FACS Vantage and maintained in fully supplemented DMEM with 1 mg/ml G-418. TC2/GFP+ cells were maintained in Dulbecco's Modified Eagle Medium (DMEM) (Invitrogen, Carlsbad, Calif.) supplemented with 10% FBS (Atlanta Biological, Lawrenceville, Ga.) and 1% antibiotic-antimycotic (Invitrogen, Carlsbad, Calif.) at 37° C. and 5% $CO_2$.

Cell Transfection

The day before transfection, cells were plated at 50,000 cells per well in 24-well plates. For transfection of cells with nanovector formulations, cells were treated with nanovectors for 8 hrs under normal growth conditions. After the 8-hour incubation the media were replaced and cells incubated for an additional 48 hrs before analyses. Transfections of cells with siRNA using Dharmafect 4 (Dharmacon, Lafayette, Colo.) were performed according to the manufacturer's instructions.

Cell Viability and Gene Silencing

Potential cytotoxicity associated with the nanovector formulations was examined by the Alamar blue assay. After treatment, cells were washed with PBS three times, and incubated for 2 hrs with 10% Alamar blue (Invitrogen) in phenol red-free DMEM (supplemented with 10% FBS and 1% antibiotic-antimycotic). The percent reduction of Alamar blue was determined following the manufacturer's protocol and used to calculate percent viability of treated samples (untreated cells represent 100% viability).

To quantify the degree of GFP gene silencing, treated cells were washed with PBS three times and lysed with 1% Triton X-100 in PBS. GFP protein expression was measured at an excitation and an emission wavelength of 488 and 520 nm, respectively. GFP fluorescence levels were normalized to the total number of viable cells, as determined by the Alamar Blue viability assay. Relative GFP expression levels were then calculated based on the reduction in GFP expression as compared to non-transfected cells.

Confocal Fluorescence Microscopy 50,000 treated cells were plated on each of 24 mm glass cover slips and allowed to attach for 24 hrs. Cells were then washed with PBS and fixed in 4% formaldehyde (Polysciences Inc., Warrington, Pa.) for 30 min. Cells were then washed three times with PBS and membrane-stained with WGA-AF647 (Invitrogen, Carlsbad, Calif.) according to the manufacturer's instructions. Cover slips were then mounted on microscope slides using Prolong Gold antifade solution (Invitrogen, Carlsbad, Calif.) containing DAPI for cell nuclei staining. Images were acquired on a LSM 510 Meta confocal fluorescence microscope (Carl Zeiss Inc., Peabody, Mass.) with the appropriate filters.

Transmission Electron Microscopy (TEM)

One million C6 cells were seeded in 25 $cm^2$ flasks 24 hrs before treatment. Cells were then treated with nanovector formulations as described for gene silencing experiments. Cells were then washed three times with PBS and incubated with ice cold Karnovsky's fixative for 24 hrs. Following the fixation, the cells were processed directly from flasks for sectioning. Cell sections were stained with osmium tetroxide, lead citrate, and uranyl acetate for TEM-contrast enhancement. Cell samples were then imaged with a Philips CM100 TEM at 100 kV with a Gatan 689 digital slow scan camera.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for silencing or reducing the expression level of a gene, comprising contacting a cancer cell of interest with a nanovector effective to silence or reduce the expression level of the gene, which comprises a nanoparticle and a therapeutic agent, wherein the nanoparticle comprises:
   (a) a core consisting of a core material and a core surface, wherein the core material is a material having magnetic resonance imaging activity;
   (b) a polyarginine coating covalently coupled to the core surface; and
   (c) a poly(alkylene oxide) oligomer intermediate the core surface and the polyarginine coating, to which the polyarginine coating is covalently bonded.

2. The method of claim 1, wherein the nanoparticle further comprises a targeting agent.

3. The method of claim 2, wherein the targeting agent is selected from the group consisting of a small organic molecule, a peptide, an aptamer, a protein, and a nucleic acid.

4. The method claim 2, wherein the nanoparticle further comprises a fluorescent agent, which is covalently attached to the nanoparticle.

5. The method of claim 1, wherein polyarginine has an average molecular weight from about 2,000 to about 200,000 g/mole.

6. The method of claim 1, wherein the therapeutic agent is selected from the group consisting of a small organic molecule, a peptide, an aptamer, a protein, and a nucleic acid.

7. The method of claim 1, wherein the therapeutic agent is an RNA or a DNA.

8. The method of claim 1, wherein the therapeutic agent is an siRNA.

9. The method of claim 1, wherein the poly(alkylene oxide) oligomer is covalently coupled to the core surface by siloxane linkages.

10. The method of claim 1, wherein the nanoparticle further comprises a fluorescent agent, which is covalently attached to the nanoparticle.

11. The method of claim 1, wherein the nanoparticle is introduced into the cancer cell via transcytosis.

12. A method for silencing or reducing the expression level of a gene, comprising contacting a cancer cell of interest with a nanovector effective to silence or reduce the expression level of the gene, which comprises a nanoparticle and a therapeutic agent, wherein the nanoparticle comprises:
   (a) a core consisting of a core material and a core surface;
   (b) a polyarginine coating covalently coupled to the core surface; and
   (c) a poly(alkylene oxide) oligomer intermediate the core surface and the polyarginine coating, to which the polyarginine coating is covalently bonded; and
   (d) a fluorescent agent covalently attached to the nanoparticle.

13. A method for silencing or reducing the expression level of a gene, comprising contacting a cancer cell of interest with a nanovector effective to silence or reduce the expression level of the gene, which comprises a nanoparticle and a therapeutic agent, wherein the nanoparticle comprises:
   (a) a core consisting of a core material and a core surface;
   (b) a polyarginine coating covalently coupled to the core surface;
   (c) a poly(alkylene oxide) oligomer intermediate the core surface and the polyarginine coating, to which the polyarginine coating is covalently bonded;
   (d) a fluorescent agent covalently attached to the nanoparticle; and
   (e) a targeting agent.

* * * * *